(12) United States Patent
Palanker et al.

(10) Patent No.: US 9,693,903 B2
(45) Date of Patent: *Jul. 4, 2017

(54) APPARATUS FOR PATTERNED PLASMA-MEDIATED LASER OPHTHALMIC SURGERY

(71) Applicant: OPTIMEDICA CORPORATION, Santa Ana, CA (US)

(72) Inventors: Daniel V. Palanker, Sunnyvale, CA (US); Mark S. Blumenkranz, Portola Valley, CA (US); David H. Mordaunt, Los Gatos, CA (US); Dan E. Andersen, Menlo Park, CA (US)

(73) Assignee: Optimedica Corporation, Santa Ana, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/236,284

(22) Filed: Aug. 12, 2016

(65) Prior Publication Data

US 2016/0346119 A1     Dec. 1, 2016

Related U.S. Application Data

(63) Continuation of application No. 14/949,645, filed on Nov. 23, 2015, now Pat. No. 9,474,648, which is a
(Continued)

(51) Int. Cl.
*A61B 18/18* (2006.01)
*A61F 9/008* (2006.01)
(Continued)

(52) U.S. Cl.
CPC ............. *A61F 9/008* (2013.01); *A61B 18/20* (2013.01); *A61B 90/361* (2016.02);
(Continued)

(58) Field of Classification Search
CPC ...................... A61F 9/008; A61F 2009/00887
(Continued)

(56) References Cited

U.S. PATENT DOCUMENTS 3,169,459 A   2/1965   Friedberg et al.
3,971,382 A   7/1976   Krasnov
(Continued)

FOREIGN PATENT DOCUMENTS

EP   0697611 A2   2/1996
EP    697611 A2   2/1996
(Continued)

OTHER PUBLICATIONS

Abstract of AU Publication No. 2007292491, Publication Date Mar. 13, 2008, which is the AU counterpart of the WO08030718 A2 application.
(Continued)

*Primary Examiner* — William Thomson
*Assistant Examiner* — Joshua Rosefelt
(74) *Attorney, Agent, or Firm* — Abbott Medical Optics Inc.

(57) ABSTRACT

A system for ophthalmic surgery on an eye includes: a pulsed laser which produces a treatment beam; an OCT imaging assembly capable of creating a continuous depth profile of the eye; an optical scanning system configured to position a focal zone of the treatment beam to a targeted location in three dimensions in one or more floaters in the posterior pole. The system also includes one or more controllers programmed to automatically scan tissues of the patient's eye with the imaging assembly; identify one or more boundaries of the one or more floaters based at least in part on the image data; iii. identify one or more treatment regions based upon the boundaries; and operate the optical scanning system with the pulsed laser to produce a treatment
(Continued)

beam directed in a pattern based on the one or more treatment regions.

18 Claims, 10 Drawing Sheets

Related U.S. Application Data continuation of application No. 14/742,663, filed on Jun. 17, 2015, now Pat. No. 9,271,870, which is a continuation of application No. 14/184,047, filed on Feb. 19, 2014, now Pat. No. 9,101,448, which is a continuation of application No. 13/558,966, filed on Aug. 17, 2012, now Pat. No. 8,709,001, which is a continuation of application No. 11/328,970, filed on Jan. 9, 2006, now Pat. No. 8,394,084.

(60) Provisional application No. 60/643,056, filed on Jan. 10, 2005.

(51) Int. Cl.
    *A61F 9/007* (2006.01)
    *A61F 9/009* (2006.01)
    *A61B 18/20* (2006.01)
    *A61F 2/16* (2006.01)
    *A61B 90/00* (2016.01)
    *A61B 18/00* (2006.01)

(52) U.S. Cl.
    CPC ............ *A61F 2/1602* (2013.01); *A61F 9/009* (2013.01); *A61F 9/0084* (2013.01); *A61F 9/00736* (2013.01); *A61F 9/00754* (2013.01); *A61F 9/00812* (2013.01); *A61F 9/00814* (2013.01); *A61F 9/00825* (2013.01); *A61F 9/00831* (2013.01); *A61F 9/00834* (2013.01); *A61F 9/00836* (2013.01); *A61F 9/00838* (2013.01); *A61B 2018/00577* (2013.01); *A61F 2009/0087* (2013.01); *A61F 2009/00844* (2013.01); *A61F 2009/00851* (2013.01); *A61F 2009/00865* (2013.01); *A61F 2009/00878* (2013.01); *A61F 2009/00882* (2013.01); *A61F 2009/00887* (2013.01); *A61F 2009/00889* (2013.01); *A61F 2009/00895* (2013.01); *A61F 2009/00897* (2013.01)

(58) Field of Classification Search
    USPC ........................................................ 606/4, 6
    See application file for complete search history.

(56) References Cited

U.S. PATENT DOCUMENTS

| | | |
|---|---|---|
| 4,169,664 A | 10/1979 | Bailey, Jr. |
| 4,309,998 A | 1/1982 | Aron et al. |
| 4,530,359 A | 7/1985 | Helfgott et al. |
| 4,538,608 A * | 9/1985 | L'Esperance, Jr. .. A61F 9/00736 372/24 |
| 4,665,913 A | 5/1987 | L'Esperance, Jr. |
| 4,907,586 A | 3/1990 | Bille et al. |
| 4,908,015 A | 3/1990 | Anis |
| 4,917,486 A | 4/1990 | Raven et al. |
| 4,995,715 A | 2/1991 | Cohen |
| 5,049,147 A | 9/1991 | Danon |
| 5,098,426 A | 3/1992 | Sklar et al. |
| 5,112,328 A | 5/1992 | Taboada et al. |
| 5,139,022 A | 8/1992 | Lempert |
| 5,139,504 A | 8/1992 | Zelman |
| 5,246,435 A * | 9/1993 | Bille ................. A61F 9/008 128/898 |
| 5,257,988 A | 11/1993 | L'Esperance, Jr. |
| 5,321,501 A | 6/1994 | Swanson et al. |
| 5,336,217 A | 8/1994 | Buys et al. |
| 5,391,165 A | 2/1995 | Fountain et al. |
| 5,403,307 A | 4/1995 | Zelman |
| 5,437,658 A | 8/1995 | Muller et al. |
| 5,439,462 A | 8/1995 | Bille et al. |
| 5,459,570 A | 10/1995 | Swanson et al. |
| 5,480,396 A | 1/1996 | Simon et al. |
| 5,491,524 A | 2/1996 | Hellmuth et al. |
| 5,493,109 A * | 2/1996 | Wei ..................... A61B 3/102 250/201.3 |
| 5,505,693 A | 4/1996 | Mackool |
| 5,520,679 A | 5/1996 | Lin |
| 5,549,632 A | 8/1996 | Lai |
| 5,620,435 A | 4/1997 | Belkin et al. |
| 5,702,441 A | 12/1997 | Zhou |
| 5,719,673 A | 2/1998 | Dorsel et al. |
| 5,720,894 A | 2/1998 | Neev et al. |
| 5,743,902 A | 4/1998 | Trost |
| 5,748,352 A | 5/1998 | Hattori |
| 5,748,898 A | 5/1998 | Ueda |
| 5,779,696 A | 7/1998 | Berry et al. |
| 5,847,827 A | 12/1998 | Fercher |
| 5,865,830 A | 2/1999 | Parel et al. |
| 5,906,611 A | 5/1999 | Dodick et al. |
| 5,919,186 A | 7/1999 | Bath |
| 5,957,915 A | 9/1999 | Trost |
| 5,971,978 A | 10/1999 | Mukai |
| 5,980,513 A | 11/1999 | Frey et al. |
| 5,984,916 A | 11/1999 | Lai |
| 5,993,438 A | 11/1999 | Juhasz et al. |
| 6,002,127 A | 12/1999 | Vestal et al. |
| 6,004,314 A | 12/1999 | Wei et al. |
| 6,010,497 A | 1/2000 | Tang et al. |
| 6,019,472 A | 2/2000 | Koester et al. |
| 6,053,613 A | 4/2000 | Wei et al. |
| 6,057,543 A | 5/2000 | Vestal et al. |
| 6,095,648 A | 8/2000 | Birngruber et al. |
| 6,099,522 A | 8/2000 | Knopp et al. |
| 6,110,166 A | 8/2000 | Juhasz |
| 6,111,645 A | 8/2000 | Tearney et al. |
| 6,146,375 A | 11/2000 | Juhasz et al. |
| 6,149,644 A | 11/2000 | Xie |
| 6,210,401 B1 | 4/2001 | Lai |
| 6,254,595 B1 | 7/2001 | Juhasz et al. |
| 6,281,493 B1 | 8/2001 | Vestal et al. |
| 6,287,299 B1 | 9/2001 | Sasnett et al. |
| 6,307,589 B1 | 10/2001 | Maquire, Jr. |
| 6,322,216 B1 | 11/2001 | Yee et al. |
| 6,322,556 B1 | 11/2001 | Gwon et al. |
| 6,324,191 B1 | 11/2001 | Horvath |
| 6,325,792 B1 | 12/2001 | Swinger et al. |
| 6,328,733 B1 | 12/2001 | Trost |
| RE37,504 E | 1/2002 | Lin |
| 6,344,040 B1 | 2/2002 | Juhasz et al. |
| RE37,585 E | 3/2002 | Mourou et al. |
| 6,373,571 B1 | 4/2002 | Juhasz et al. |
| 6,396,587 B1 | 5/2002 | Knupfer et al. |
| D459,806 S | 7/2002 | Webb |
| D459,807 S | 7/2002 | Webb |
| D462,442 S | 9/2002 | Webb |
| D462,443 S | 9/2002 | Webb |
| 6,454,761 B1 | 9/2002 | Freedman |
| 6,485,413 B1 | 11/2002 | Boppart et al. |
| 6,497,701 B2 | 12/2002 | Shimmick et al. |
| 6,544,254 B1 | 4/2003 | Bath |
| 6,585,723 B1 | 7/2003 | Sumiya |
| 6,605,093 B1 | 8/2003 | Blake |
| 6,610,050 B2 | 8/2003 | Bille |
| 6,620,154 B1 | 9/2003 | Amirkhanian et al. |
| 6,623,476 B2 | 9/2003 | Kurtz et al. |
| 6,635,051 B1 | 10/2003 | Hohla |
| 6,638,271 B2 | 10/2003 | Munnerlyn et al. |
| 6,648,877 B1 | 11/2003 | Juhasz et al. |
| 6,652,511 B1 | 11/2003 | Tomita |
| 6,676,653 B2 | 1/2004 | Juhasz et al. |
| 6,693,927 B1 | 2/2004 | Horvath et al. |
| 6,706,036 B2 | 3/2004 | Lai |
| 6,751,033 B2 | 6/2004 | Goldstein et al. |

(56) References Cited

U.S. PATENT DOCUMENTS

| | | |
|---|---|---|
| 6,887,231 B2 | 5/2005 | Mrochen et al. |
| 6,902,561 B2 | 6/2005 | Kurtz et al. |
| 7,027,233 B2 | 4/2006 | Goldstein et al. |
| 7,101,364 B2 | 9/2006 | Bille |
| 7,146,983 B1 | 12/2006 | Hohla et al. |
| 7,217,266 B2 | 5/2007 | Anderson et al. |
| 7,246,905 B2 | 7/2007 | Benedikt et al. |
| 7,351,241 B2 | 4/2008 | Bendett et al. |
| 7,655,002 B2 | 2/2010 | Myers et al. |
| 7,717,907 B2 | 5/2010 | Ruiz et al. |
| 8,092,446 B2 | 1/2012 | Bischoff et al. |
| 8,186,357 B2 | 5/2012 | Lubatschowski et al. |
| 8,262,646 B2 | 9/2012 | Frey et al. |
| 8,350,183 B2 | 1/2013 | Vogel et al. |
| 8,382,745 B2 | 2/2013 | Naranjo-Tackman et al. |
| 8,403,921 B2 | 3/2013 | Blumenkranz et al. |
| 8,414,564 B2 | 4/2013 | Goldshleger et al. |
| 8,709,001 B2 | 4/2014 | Blumenkranz et al. |
| 8,808,279 B2 | 8/2014 | Muhlhoff et al. |
| 2002/0100990 A1 | 8/2002 | Platt et al. |
| 2002/0103478 A1 | 8/2002 | Gwon et al. |
| 2002/0128637 A1 | 9/2002 | Von Der Heide et al. |
| 2002/0198516 A1 | 12/2002 | Knopp et al. |
| 2003/0053219 A1 | 3/2003 | Manzi |
| 2003/0060880 A1 | 3/2003 | Feingold |
| 2003/0098834 A1 | 5/2003 | Ide et al. |
| 2003/0125718 A1 | 7/2003 | Munnerlyn et al. |
| 2003/0220629 A1 | 11/2003 | Bille et al. |
| 2004/0002695 A1* | 1/2004 | Youssefi ............... A61F 9/008 606/5 |
| 2004/0054358 A1 | 3/2004 | Cox |
| 2004/0082864 A1 | 4/2004 | Barbato |
| 2004/0148022 A1 | 7/2004 | Eggleston |
| 2004/0199150 A1 | 10/2004 | Lai |
| 2004/0243112 A1 | 12/2004 | Bendett et al. |
| 2005/0107773 A1 | 5/2005 | Bergt et al. |
| 2005/0286019 A1 | 12/2005 | Wiltberger et al. |
| 2005/0288745 A1 | 12/2005 | Andersen et al. |
| 2006/0100677 A1 | 5/2006 | Blumenkranz et al. |
| 2006/0106372 A1 | 5/2006 | Kuhn et al. |
| 2006/0195076 A1 | 8/2006 | Blumenkranz et al. |
| 2006/0235428 A1 | 10/2006 | Silvestrini |
| 2007/0173794 A1 | 7/2007 | Frey et al. |
| 2007/0173795 A1 | 7/2007 | Frey et al. |
| 2008/0058704 A1 | 3/2008 | Hee et al. |
| 2008/0058841 A1 | 3/2008 | Kurtz et al. |
| 2008/0161781 A1 | 7/2008 | McArdle et al. |
| 2008/0281303 A1 | 11/2008 | Culbertson et al. |
| 2008/0281413 A1 | 11/2008 | Culbertson et al. |
| 2009/0012507 A1 | 1/2009 | Culbertson et al. |
| 2010/0137850 A1 | 6/2010 | Culbertson et al. |
| 2010/0137982 A1 | 6/2010 | Culbertson et al. |
| 2010/0137983 A1 | 6/2010 | Culbertson et al. |
| 2010/0191226 A1 | 7/2010 | Blumenkranz et al. |
| 2011/0178511 A1 | 7/2011 | Blumenkranz et al. |
| 2011/0178512 A1 | 7/2011 | Blumenkranz et al. |
| 2011/0319873 A1 | 12/2011 | Raksi et al. |
| 2011/0319875 A1 | 12/2011 | Loesel et al. |
| 2014/0336627 A1 | 11/2014 | Kempe et al. |
| 2015/0038952 A1 | 2/2015 | Blumenkranz et al. |

FOREIGN PATENT DOCUMENTS

| | | | |
|---|---|---|---|
| EP | 1279386 | A1 | 1/2003 |
| EP | 1364632 | A1 | 11/2003 |
| JP | 2003052737 | A | 2/2003 |
| WO | 9009141 | A2 | 8/1990 |
| WO | 9105515 | A1 | 5/1991 |
| WO | 9308677 | A2 | 5/1993 |
| WO | 9308877 | A1 | 5/1993 |
| WO | 9316631 | A1 | 9/1993 |
| WO | 9407424 | A1 | 4/1994 |
| WO | 9409849 | A1 | 5/1994 |
| WO | 2004026198 | A2 | 4/2004 |
| WO | 2004026198 | A3 | 11/2004 |
| WO | 2004105660 | A1 | 12/2004 |
| WO | 2008030718 | A2 | 3/2008 |
| WO | 2008030718 | A3 | 12/2008 |

OTHER PUBLICATIONS

Andreo L K., et al., "Elastic Properties and Scanning Electron Microscopic Appearance of Manual Continuous Curvilinear Capsulorhexis and Vitrectorhexis in an Animal Model of Pediatric Cataract," Journal of Cataract and Refractive Surgery, 1999, vol. 25 (4), pp. 534-539.

Baikoff G., et al., "Contact Between 3 Phakic Intraocular Lens Models and the Crystalline Lens: An Anterior chamber Optical Coherence Tomography Study," Journal of Cataract and Refractive Surgery, 2004, vol. 30 (9), pp. 2007-2012.

Bloembergen N., et al., "Laser-Induced Electric Breakdown in Solids," IEEE Journal of Quantum Electronics, 1974, vol. 10 (3), pp. 375-386.

Culbertson W.W., "Femtosecond Assisted Laser Cataract Extradition," Presented at the International Congress on Surface Ablation, Femto-Lasers & Cross-Linking, May 2010, 33 pages.

European Search Report for Application No. EP12177880, mailed on Mar. 4, 2013, 6 pages.

European Search Report for Application No. EP13170944, mailed on Oct. 17, 2013, 5 pages.

European Search Report for Application No. EP16157063, mailed on Jun. 22, 2016, 7 pages.

European Search Report for Application No. EP16157067, mailed on Jun. 22, 2016, 6 pages.

Fradin D.W., et al., "Dependence of Laser-Induced Breakdown Field Strength on Pulse Duration," Applied Physics Letters, 1973, vol. 22 (12), pp. 635-637.

Frey R.W., et al., "Evaluations of the Mechanical Properties of the Crystalline Lens Capsule Following Photodistribution Capsulotomy and Continuous Curvilinear Capsulorhexis," Investigative Ophthalmology & Visual Science, 2009, vol. 50, pp. E-Abstract 1141.

Friedman N.J., et al., "Femtosecond Laser Capsulotomy," Journal of Cataract and Refractive Surgery, 2011, vol. 37 (7), pp. 1189-1198.

Geerling G., et al., "Initial Clinical Experience with the Picosecond Nd:YLF Laser for Intraocular Therapeutic Applications," British Journal of Ophthalmology, 1998, vol. 82 (5), pp. 504-509.

Gimbel H.V., et al., "Continuous Curvilinear Capsulorhexis," Journal of Cataract and Refractive Surgery, 1991, vol. 17 (1), pp. 110-111.

Gimbel H.V., et al., "Development, Advantages and Methods of the Continuous Circular Capsulorhexis Technique," Journal of Cataract and Refractive Surgery, 1990, vol. 16 (1), pp. 31-37.

Gimbel H.V., et al., "Principles of Nuclear Phaco Emulsification" In: Cataract Surgery Techniques Complications and Management, 2nd edition., Steinert et al., 2004, Chap. 15, pp. 153-181.

International Search Report and Written Opinion for Application No. PCT/US06/00873, mailed on Aug. 9, 2007, 7 pages.

Izatt J.A., et al., "Micrometer-Scale Resolution Imaging of the Anterior Eye In Vivo With Optical Coherence Tomography," Arch Ophthalmology, 1994, vol. 112 (12), pp. 1584-1589.

Loesel F.H., et al., "Effect of Reduction of Laser Pulse Width from 100 ps to 20 fs on the Plasma-Mediated Ablation of Hard and Soft Tissue," Proceedings of the SPIE, 1999, vol. 3565, pp. 116-123.

Loesel F.H., et al., "Laser-Induced Optical Breakdown on Hard and Soft Tissues and its Dependence on the Pulse Duration: Experiment and Model," IEEE Journal of Quantum Electronics, 1996, vol. 32 (10), pp. 1717-1722.

Luck J., et al., "A Comparative Study of the Elastic Properties of Continuous Tear Curvilinear Capsulorhexis Versus Capsulorhexis Produced by Radiofrequency Endodiathermy," British Journal of Ophthalmology, 1994, vol. 78 (5), pp. 392-396.

Morgan J.E., et al., "The Mechanical Properties of the Human Lens Capsule Following Capsulorhexis or Radiofrequency Diathermy Capsulotomy," Archives of Ophthalmology, 1996, vol. 114 (9), pp. 1110-1115.

(56) References Cited

OTHER PUBLICATIONS

Nagy Z., et al., "Initial Clinical Evaluation of an Intraocular Femtosecond Laser in Cataract Surgery," Journal of Refractive Surgery, 2009, vol. 25 (12), pp. 1053-1060.
Niemz M.H., "Laser-Tissure Interactions—Fundamentals and Applications" 3rd edition, Springer Press, 2003.
Palanker D.V., et al., "Femtosecond Laser-Assisted Cataract Surgery with Integrated Optical Coherence Tomography," Science Translational Medicine, 2010, vol. 2 (58), pp. 58ra85.
Schmitt J.M., et al., "Optical Coherence Tomography (OCT): A Review," IEEE Journal of Selected Topics in Quantum Electronics, 1999, vol. 5 (4), pp. 1205-1215.
Schuele G., et al., "Capsular Strength and Ultrastructural Appearance of Femtosecond Laser Capsulotomy and Manual Capsulorhexis," Investigative Ophthalmology & Visual Science, 2011, vol. 52, pp. E-Abstract 5704.
Steinert et al., "Neodymium: Yttrium-Aluminum-Garnet Laser Posterior Capsulotomy," in: Cataract Surgery Techniques Complications and Management, 2nd edition., Steinert et al., 2004, Chapter. 44, pp. 531-544.
Stern D., et al., "Corneal Ablation by Nanosecond, Picosecond, and Femtosecond Lasers at 532 and 625 nm," Archives of Opthalmology, 1989, vol. 107 (4), pp. 587-592.
Sun H., et al., "Femtosecond Laser Corneal Ablation Threshold: Dependence on Tissue Depth and Laser Pulse Width," Lasers in Surgery and Medicine, 2007, vol. 39 (8), pp. 654-658.
Supplementary European Search Report for Application No. EP06718001, mailed on Mar. 4, 2010, 10 pages.
Trivedi R.H., et al., "Extensibility and Scanning Electron Microscopy Evaluation of 5 Pediatric Anterior Capsulotomy Techniques in a Porcine Model," Journal of Cataract and Refractive Surgery, 2006, vol. 32 (7), pp. 1206-1213.
Vogel A., et al., "Optical Breakdown in Water and Ocular Media and its Use for Intraocular Photodisruption" Shaker Verlag GmbH, 2001.
Wilson M.E., "Anterior Lens Capsule Management in Pediatric Cataract Surgery," Transactions of the Ophthalmological Society, 2004, vol. 102, pp. 391-422.

* cited by examiner

APPARATUS FOR PATTERNED PLASMA-MEDIATED LASER OPHTHALMIC SURGERY

CROSS-REFERENCE

This application claims priority to and is a continuation of U.S. patent application Ser. No. 14/949,645, filed Nov. 23, 2015, which is a continuation of U.S. patent application Ser. No. 14/742,663, filed Jun. 17, 2015, which is a continuation of U.S. patent application Ser. No. 14/184,047, filed Feb. 19, 2014, which is a continuation of U.S. patent application Ser. No. 13/588,966, filed Aug. 17, 2012, which is a continuation of U.S. patent application Ser. No. 11/328,970, filed Jan. 9, 2006, which claims the benefit under 35 U.S.C. §119(e) of U.S. Provisional Patent Application No. 60/643,056, filed Jan. 10, 2005, the full disclosures of which are incorporated herein by reference.

FIELD OF THE INVENTION

The present invention relates to ophthalmic surgical procedures and systems.

BACKGROUND OF THE INVENTION

Cataract extraction is one of the most commonly performed surgical procedures in the world with estimates of 2.5 million cases being performed annually in the United States and 9.1 million cases worldwide. This is expected to increase to approximately 13.3 million cases by 2006 globally. This market is composed of various segments including intraocular lenses for implantation, viscoelastic polymers to facilitate surgical maneuvers, disposable instrumentation including ultrasonic phacoemulsification tips, tubing, and various knives and forceps. Modern cataract surgery is typically performed using a technique termed phacoemulsification in which an ultrasonic tip with an associated water stream for cooling purposes is used to sculpt the relatively hard nucleus of the lens after performance of an opening in the anterior lens capsule termed anterior capsulotomy or more recently capsulorhexis. Following these steps as well as removal of residual softer lens cortex by aspiration methods without fragmentation, a synthetic foldable intraocular lens (IOL's) inserted into the eye through a small incision. This technique is associated with a very high rate of anatomic and visual success exceeding 95% in most cases and with rapid visual rehabilitation.

One of the earliest and most critical steps in the procedure is the performance of capsulorhexis. This step evolved from an earlier technique termed can-opener capsulotomy in which a sharp needle was used to perforate the anterior lens capsule in a circular fashion followed by the removal of a circular fragment of lens capsule typically in the range of 5-8 mm in diameter. This facilitated the next step of nuclear sculpting by phacoemulsification. Due to a variety of complications associated with the initial can-opener technique, attempts were made by leading experts in the field to develop a better technique for removal of the anterior lens capsule preceding the emulsification step. These were pioneered by Neuhann, and Gimbel and highlighted in a publication in 1991 (Gimbel, Neuhann, Development Advantages and Methods of the Continuous Curvilinear Capsulorhexis. *Journal of Cataract and Refractive Surgery* 1991; 17:110-111, incorporated herein by reference). The concept of the capsulorhexis is to provide a smooth continuous circular opening through which not only the phacoemulsification of the nucleus can be performed safely and easily, but also for easy insertion of the intraocular lens. It provides both a clear central access for insertion, a permanent aperture for transmission of the image to the retina by the patient, and also a support of the IOL inside the remaining capsule that would limit the potential for dislocation.

Using the older technique of can-opener capsulotomy, or even with the continuous capsulorhexis, problems may develop related to inability of the surgeon to adequately visualize the capsule due to lack of red reflex, to grasp it with sufficient security, to tear a smooth circular opening of the appropriate size without radial rips and extensions or technical difficulties related to maintenance of the anterior chamber depth after initial opening, small size of the pupil, or the absence of a red reflex due to the lens opacity. Some of the problems with visualization have been minimized through the use of dyes such as methylene blue or indocyanine green. Additional complications arise in patients with weak zonules (typically older patients) and very young children that have very soft and elastic capsules, which are very difficult to mechanically rupture.

Finally, during the intraoperative surgical procedure, and subsequent to the step of anterior continuous curvilinear capsulorhexis, which typically ranges from 5-7 mm in diameter, and prior to IOL insertion the steps of hydrodissection, hydrodilineation and phaco emulsification occur. These are intended to identify and soften the nucleus for the purposes of removal from the eye. These are the longest and thought to be the most dangerous step in the procedure due to the use of pulses of ultrasound that may lead to inadvertent ruptures of the posterior lens capsule, posterior dislocation of lens fragments, and potential damage anteriorly to the corneal endothelium and/or iris and other delicate intraocular structures. The central nucleus of the lens, which undergoes the most opacification and thereby the most visual impairment, is structurally the hardest and requires special techniques. A variety of surgical maneuvers employing ultrasonic fragmentation and also requiring considerable technical dexterity on the part of the surgeon have evolved, including sculpting of the lens, the so-called "divide and conquer technique" and a whole host of similarly creatively named techniques, such as phaco chop, etc. These are all subject to the usual complications associated with delicate intraocular maneuvers (Gimbel. Chapter 15: Principles of Nuclear PhacoEmulsification. *In Cataract Surgery Techniques Complications and Management*. $2^{nd}$ ed. Edited by Steinert et al. 2004: 153-181, incorporated herein by reference.).

Following cataract surgery one of the principal sources of visual morbidity is the slow development of opacities in the posterior lens capsule, which is generally left intact during cataract surgery as a method of support for the lens, to provide good centration of the IOL, and also as a means of preventing subluxation posteriorly into the vitreous cavity. It has been estimated that the complication of posterior lens capsule opacification occurs in approximately 28-50% of patients (Steinert and Richter. Chapter 44. *In Cataract Surgery Techniques Complications and Management*. $2^{nd}$ ed. Edited by Steinert et al. 2004: pg. 531-544 and incorporated herein by reference). As a result of this problem, which is thought to occur as a result of epithelial and fibrous metaplasia along the posterior lens capsule centrally from small islands of residual epithelial cells left in place near the equator of the lens, techniques have been developed initially using surgical dissection, and more recently the neodymium YAG laser to make openings centrally in a non-invasive fashion. However, most of these techniques can still be considered relatively primitive requiring a high degree of manual dexterity on the part of the surgeon and the creation of a series of high energy pulses in the range of 1 to 10 mJ manually marked out on the posterior lens capsule, taking great pains to avoid damage to the intraocular lens. The course nature of the resulting opening is illustrated clearly in FIG. 44-10, pg. 537 of Steinert and Richter, Chapter 44 of *In Cataract Surgery Techniques Complications and Management. 2nd ed* (see complete cite above).

What is needed are ophthalmic methods, techniques and apparatus to advance the standard of care of cataract and other ophthalmic pathologies.

SUMMARY OF THE INVENTION

The techniques and system disclosed herein provide many advantages. Specifically, rapid and precise openings in the lens capsule and fragmentation of the lens nucleus and cortex is enabled using 3-dimensional patterned laser cutting. The duration of the procedure and the risk associated with opening the capsule and fragmentation of the hard nucleus are reduce, while increasing precision of the procedure. The removal of a lens dissected into small segments is performed using a patterned laser scanning and just a thin aspiration needle. The removal of a lens dissected into small segments is performed using patterned laser scanning and using a ultrasonic emulsifier with a conventional phacoemulsification technique or a technique modified to recognize that a segmented lens will likely be more easily removed (i.e., requiring less surgical precision or dexterity) and/or at least with marked reduction in ultrasonic emulsification power, precision and/or duration. There are surgical approaches that enable the formation of very small and geometrically precise opening(s) in precise locations on the lens capsule, where the openings in the lens capsule would be very difficult if not impossible to form using conventional, purely manual techniques. The openings enable greater precision or modifications to conventional ophthalmic procedures as well as enable new procedures. For example, the techniques described herein may be used to facilitate anterior and/or posterior lens removal, implantation of injectable or small foldable IOLs as well as injection of compounds or structures suited to the formation of accommodating IOLs.

Another procedure enabled by the techniques described herein provides for the controlled formation of a hemicircular or curvilinear flap in the anterior lens surface. Contrast to conventional procedures which require a complete circle or nearly complete circular cut. Openings formed using conventional, manual capsulorhexis techniques rely primarily on the mechanical shearing properties of lens capsule tissue and uncontrollable tears of the lens capsule to form openings. These conventional techniques are confined to the central lens portion or to areas accessible using mechanical cutting instruments and to varying limited degrees utilize precise anatomical measurements during the formation of the tears. In contrast, the controllable, patterned laser techniques described herein may be used to create a semi-circular capsular flap in virtually any position on the anterior lens surface and in virtually any shape. They may be able to seal spontaneously or with an autologous or synthetic tissue glue or other method. Moreover, the controllable, patterned laser techniques described herein also have available and/or utilize precise lens capsule size, measurement and other dimensional information that allows the flap or opening formation while minimizing impact on surrounding tissue. The flap is not limited only to semi-circular but may be any shape that is conducive to follow on procedures such as, for example, injection or formation of complex or advanced IOL devices or so called injectable polymeric or fixed accommodating IOLs.

The techniques disclosed herein may be used during cataract surgery to remove all or a part of the anterior capsule, and may be used in situations where the posterior capsule may need to be removed intraoperatively, for example, in special circumstances such as in children, or when there is a dense posterior capsular opacity which can not be removed by suction after the nucleus has been removed. In the first, second and third years after cataract surgery, secondary opacification of the posterior lens capsule is common and is benefited by a posterior capsulotomy which may be performed or improved utilizing aspects of the techniques disclosed herein.

Because of the precision and atraumatic nature of incisions formed using the techniques herein, it is believed that new meaning is brought to minimally invasive ophthalmic surgery and lens incisions that may be self healing.

In one aspect, a method of making an incision in eye tissue includes generating a beam of light, focusing the beam at a first focal point located at a first depth in the eye tissue, scanning the beam in a pattern on the eye while focused at the first depth, focusing the beam at a second focal point located at a second depth in the eye tissue different than the first depth, and scanning the beam in the pattern on the eye while focused at the second depth.

In another aspect, a method of making an incision in eye tissue includes generating a beam of light, and passing the beam through a multi-focal length optical element so that a first portion of the beam is focused at a first focal point located at a first depth in the eye tissue and a second portion of the beam is focused at a second focal point located at a second depth in the eye tissue different than first depth.

In yet another aspect, a method of making an incision in eye tissue includes generating a beam of light having at least a first pulse of light and a second pulse of light, and focusing the first and second pulses of light consecutively into the eye tissue, wherein the first pulse creates a plasma at a first depth within the eye tissue, and wherein the second pulse arrives before the plasma disappears and is absorbed by the plasma to extend the plasma in the eye tissue along the beam.

In yet one more aspect, a method of making an incision in eye tissue includes generating a beam of light, and focusing the light into the eye tissue to create an elongated column of focused light within the eye tissue, wherein the focusing includes subjecting the light to at least one of a non-spherical lens, a highly focused lens with spherical aberrations, a curved mirror, a cylindrical lens, an adaptive optical element, a prism, and a diffractive optical element.

In another aspect, a method of removing a lens and debris from an eye includes generating a beam of light, focusing the light into the eye to fragment the lens into pieces, removing the pieces of lens, and then focusing the light into the eye to ablate debris in the eye.

In one more aspect, a method of removing a lens from a lens capsule in an eye includes generating a beam of light, focusing the light into the eye to form incisions in the lens capsule, inserting an ultrasonic probe through the incision and into the lens capsule to break the lens into pieces, removing the lens pieces from the lens capsule, rinsing the lens capsule to remove endothermial cells therefrom, and inserting at least one of a synthetic. foldable intraocular lens or an optically transparent gel into the lens capsule.

In another aspect, an ophthalmic surgical system for treating eye tissue includes a light source for generating a beam of light, a delivery system for focusing the beam onto the eye tissue, a controller for controlling the light source and the delivery system such that the light beam is focused at multiple focal points in the eye tissue at multiple depths within the eye tissue.

In yet another aspect, an ophthalmic surgical system for treating eye tissue includes a light source for generating a beam of light having at least a first pulse of light and a second pulse of light, a delivery system for focusing the beam onto the eye tissue, a controller for controlling the light source and the delivery system such that the first and second pulses of light are consecutively focused onto the eye tissue, wherein the first pulse creates a plasma at a first depth within the eye tissue, and wherein the second pulse is arrives before the plasma disappears and absorbed by the plasma to extend the plasma in the eye tissue along the beam.

In one more aspect, an ophthalmic surgical system for treating eye tissue includes a light source for generating a beam of light, a delivery system for focusing the beam onto the eye tissue, the delivery system including at least one of a non-spherical lens, a highly focused lens with spherical aberrations, a curved mirror, a cylindrical lens, an adaptive optical element, a prism, and a diffractive optical element, and a controller for controlling the light source and the delivery system such that an elongated column of focused light within the eye tissue is created.

Other objects and features of the present invention will become apparent by a review of the specification, claims and appended figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE PREFERRED EMBODIMENTS

Figure 1:
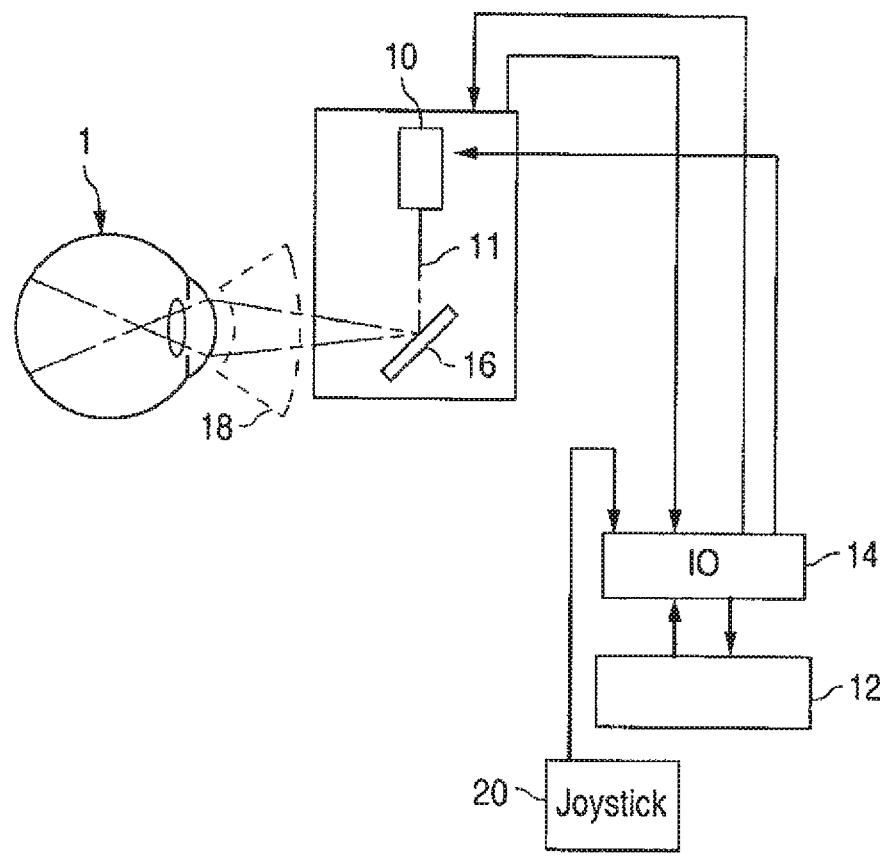
FIG. 1 is a plan diagram of a system that projects or scans an optical beam into a patient's eye.

The present invention can be implemented by a system that projects or scans an optical beam into a patient's eye 1, such as the system shown in FIG. 1. The system includes a light source 10 (e.g. laser, laser diode, etc.), which may be controlled by control electronics 12, via an input and output device 14, to create optical beam 11 (either cw or pulsed). Control electronics 12 may be a computer, microcontroller, etc. Scanning may be achieved by using one or more moveable optical elements (e.g. lenses, gratings, or as shown in FIG. 1 a mirror(s) 16) which also may be controlled by control electronics 12, via input and output device 14. Mirror 16 may be tilted to deviate the optical beam 11 as shown in FIG. 1, and direct beam 11 towards the patient's eye 1. An optional ophthalmic lens 18 can be used to focus the optical beam 11 into the patient's eye 1. The positioning and character of optical beam 11 and/or the scan pattern it forms on the eye may be further controlled by use of an input device 20 such as a joystick, or any other appropriate user input device.

Techniques herein include utilizing a light source 10 such as a surgical laser configured to provide one or more of the following parameters:

1) pulse energy up to 1 µJ repetition rate up to 1 MHz, pulse duration <1 ps 2) pulse energy up to 10 µJ rep. rate up to 100 kHz, pulse duration <1 ps.

3) Pulse energy up to 1000 µJ, rep rate up to 1 kHz, pulse duration <3 ps.

Additionally, the laser may use wavelengths in a variety of ranges including in the near-infrared range: 800-1100 nm. In one aspect, near-infrared wavelengths are selected because tissue absorption and scattering is reduced. Additionally, a laser can be configured to provide low energy ultrashort pulses of near-infrared radiation with pulse durations below 10 ps or below 1 ps, alone or in combination with pulse energy not exceeding 100 µJ, at high repetition rate including rates above 1 kHz, and above 10 kHz.

Figure 2:
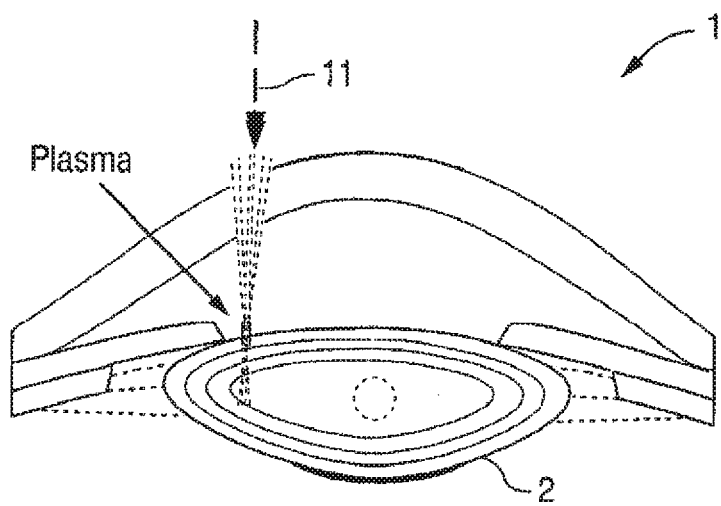
FIG. 2 is a diagram of the anterior chamber of the eye and the laser beam producing plasma at the focal point on the lens capsule.

Short pulsed laser light focused into eye tissue 2 will produce dielectric breakdown at the focal point, rupturing the tissue 2 in the vicinity of the photo-induced plasma (see FIG. 2). The diameter d of the focal point is given by $d=\lambda F/D_b$, where F is the focal length of the last focusing element, $D_b$ is the beam diameter on the last lens, and $\lambda$ is the wavelength. For a focal length F=160 mm, beam diameter on the last lens $D_b$=10 mm, and wavelength $\lambda$=1.04 um, the focal spot diameter will be $d \approx \lambda/(2.NA) \approx \lambda F/D_b = 15$ µm, where the numerical aperture of the focusing optics, $NA \approx D_b/(2F)$.

Figure 3:
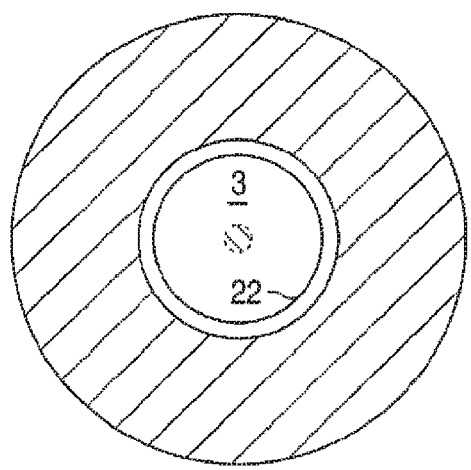
FIG. 3 is a planar view of the iris and lens with a circular pattern for the anterior capsulotomy (capsulorexis).

To provide for continuous cutting, the laser spots should not be separated by more than a width of the crater produced by the laser pulse in tissue. Assuming the rupture zone being R=15 µm (at low energies ionization might occur in the center of the laser spot and not expand to the full spot size), and assuming the maximal diameter of the capsulotomy circle being $D_c$=8 mm, the number of required pulses will be: $N=\pi D_c/R=1675$ to provide a circular cut line 22 around the circumference of the eye lens 3 as illustrated in FIG. 3. For smaller diameters ranging from 5-7 mm, the required number of pulses would be less. If the rupture zone were larger (e.g. 50 µm), the number of pulses would drop to N=503.

To produce an accurate circular cut, these pulses should be delivered to tissue over a short eye fixation time. Assuming the fixation time t=0.2 s, laser repetition rate should be: r=N/t=8.4 kHz. If the fixation time were longer, e.g. 0.5 s, the required rep. rate could be reduced to 3.4 kHz. With a rupture zone of 50 µm the rep. rate could further drop to 1 kHz.

Threshold radiant exposure of the dielectric breakdown with 4 ns pulses is about $\Phi$=100 J/cm². With a focal spot diameter being d=15 µm, the threshold pulse energy will be $E_{th}=\Phi*\pi d^2/4=176$ µJ. For stable and reproducible operation, pulse energy should exceed the threshold by at least a factor of 2, so pulse energy of the target should be E=352 µJ. The creation of a cavitation bubble might take up to 10% of the pulse energy, i.e. $E_b$=35 µJ. This corresponds to a bubble diameter $$d_b = \sqrt[3]{\frac{6E_b}{\pi P_a}} = 48 \text{ µm}.$$

The energy level can be adjusted to avoid damage to the corneal endothelium. As such, the threshold energy of the dielectric breakdown could be minimized by reducing the pulse duration, for example, in the range of approximately 0.1-1 ps. Threshold radiant exposure, $\Phi$, for dielectric breakdown for 100 fs is about $\Phi$=2 J/cm²; for 1 ps it is $\Phi$=2.5 J/cm². Using the above pulse durations, and a focal spot diameter d=15 µm, the threshold pulse energies will be $E_{th}=\Phi*\pi d^2/4$=3.5 and 4.4 µJ for 100 fs and 1 ps pulses, respectively. The pulse energy could instead be selected to be a multiple of the threshold energy, for example, at least a factor of 2. If a factor of 2 is used, the pulse energies on the target would be $E_{th}$=7 and 9 µJ, respectively. These are only two examples. Other pulse energy duration times, focal spot sizes and threshold energy levels are possible and are within the scope of the present invention.

A high repetition rate and low pulse energy can be utilized for tighter focusing of the laser beam. In one specific example, a focal distance of F=50 mm is used while the beam diameter remains $D_b$=10 mm, to provide focusing into a spot of about 4 µm in diameter. Aspherical optics can also be utilized. An 8 mm diameter opening can be completed in a time of 0.2 s using a repetition rate of about 32 kHz.

The laser 10 and controller 12 can be set to locate the surface of the capsule and ensure that the beam will be focused on the lens capsule at all points of the desired opening. Imaging modalities and techniques described herein, such as for example, Optical Coherence Tomography (OCT) or ultrasound, may be used to determine the location and measure the thickness of the lens and lens capsule to provide greater precision to the laser focusing methods, including 2D and 3D patterning. Laser focusing may also be accomplished using one or more methods including direct observation of an aiming beam, Optical Coherence Tomography (OCT), ultrasound, or other known ophthalmic or medical imaging modalities and combinations thereof.

Figure 4:
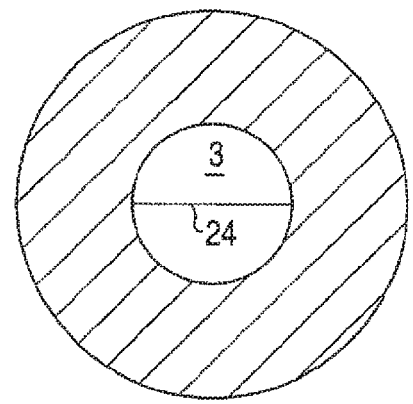
FIG. 4 is a diagram of the line pattern applied across the lens for OCT measurement of the axial profile of the anterior chamber.

As shown in FIG. 4, OCT imaging of the anterior chamber can be performed along a simple linear scan 24 across the lens using the same laser and/or the same scanner used to produce the patterns for cutting. This scan will provide information about the axial location of the anterior and posterior lens capsule, the boundaries of the cataract nucleus, as well as the depth of the anterior chamber. This information may then be loaded into the laser 3-D scanning system, and used to program and control the subsequent laser assisted surgical procedure. The information may be used to determine a wide variety of parameters related to the procedure such as, for example, the upper and lower axial limits of the focal planes for cutting the lens capsule and segmentation of the lens cortex and nucleus, the thickness of the lens capsule among others. The imaging data may be averaged across a 3-line pattern as shown in FIG. 9.

Figure 20:
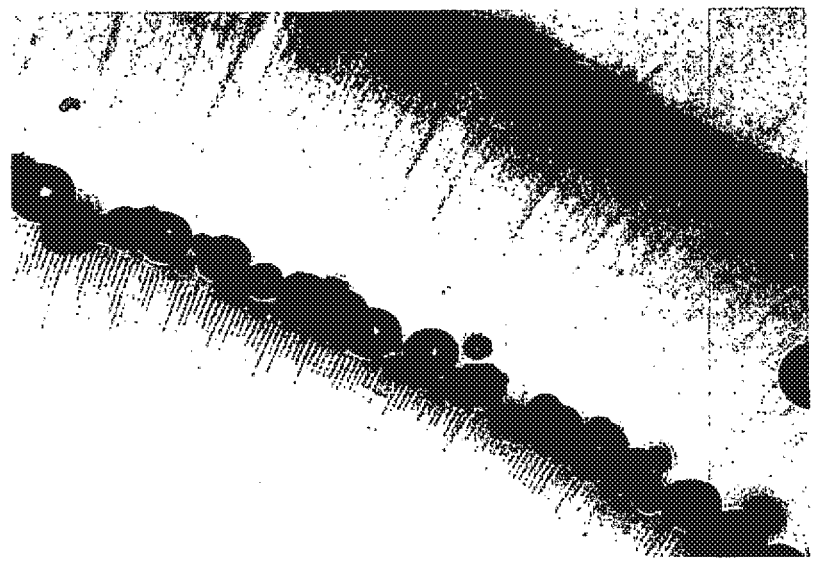
FIG. 20 illustrates fragmentation patterns of an ocular lens produced by one embodiment of the present invention.
Figure 21:
FIG. 21 illustrates circular incisions of an ocular lens produced by one embodiment of the present invention.

An example of the results of such a system on an actual human crystalline lens is shown in FIG. 20. A beam of 10 µJ, 1 ps pulses delivered at a pulse repetition rate of 50 kHz from a laser operating at a wavelength of 1045 nm was focused at NA=0.05 and scanned from the bottom up in a pattern of 4 circles in 8 axial steps. This produced the fragmentation pattern in the ocular lens shown in FIG. 20. FIG. 21 shows in detail the resultant circular incisions, which measured ~10 µm in diameter, and ~100 µm in length.

FIG. 2 illustrates an exemplary illustration of the delineation available using the techniques described herein to anatomically define the lens. As can be seen in FIG. 2, the capsule boundaries and thickness, the cortex, epinucleus and nucleus are determinable. It is believed that OCT imaging may be used to define the boundaries of the nucleus, cortex and other structures in the lens including, for example, the thickness of the lens capsule including all or a portion of the anterior or posterior capsule. In the most general sense, one aspect of the present invention is the use of ocular imaging data obtained as described herein as an input into a laser scanning and/or pattern treatment algorithm or technique that is used to as a guide in the application of laser energy in novel laser assisted ophthalmic procedures. In fact, the imaging and treatment can be performed using the same laser and the same scanner. While described for use with lasers, other energy modalities may also be utilized.

It is to be appreciated that plasma formation occurs at the waist of the beam. The axial extent of the cutting zone is determined by the half-length L of the laser beam waist, which can be expressed as: $L \sim \lambda/(4 \cdot NA^2) = dF/D_b$. Thus the lower the NA of the focusing optics, the longer waist of the focused beam, and thus a longer fragmentation zone can be produced. For F=160 mm, beam diameter on the last lens $D_b$=10 mm, and focal spot diameter d=15 µm, the laser beam waist half-length L would be 240 µm.

Figure 5:
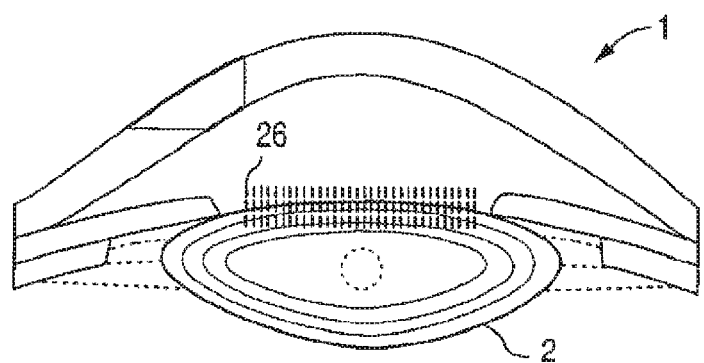
FIG. 5 is a diagram of the anterior chamber of the eye and the 3-dimensional laser pattern applied across the lens capsule.

With reference to FIG. 5, a three dimensional application of laser energy 26 can be applied across the capsule along the pattern produced by the laser-induced dielectric breakdown in a number of ways such as, for example:

1) Producing several circular or other pattern scans consecutively at different depths with a step equal to the axial length of the rupture zone. Thus, the depth of the focal point (waist) in the tissue is stepped up or down with each consecutive scan. The laser pulses are sequentially applied to the same lateral pattern at different depths of tissue using, for example, axial scanning of the focusing elements or adjusting the optical power of the focusing element while, optionally, simultaneously or sequentially scanning the lateral pattern. The adverse result of laser beam scattering on bubbles, cracks and/or tissue fragments prior to reaching the focal point can be avoided by first producing the pattern/focusing on the maximal required depth in tissue and then, in later passes, focusing on more shallow tissue spaces. Not only does this "bottom up" treatment technique reduce unwanted beam attenuation in tissue above the target tissue layer, but it also helps protect tissue underneath the target tissue layer. By scattering the laser radiation transmitted beyond the focal point on gas bubbles, cracks and/or tissue fragments which were produced by the previous scans, these defects help protect the underlying retina. Similarly, when segmenting a lens, the laser can be focused on the most posterior portion of the lens and then moved more anteriorly as the procedure continues.

Figure 6:
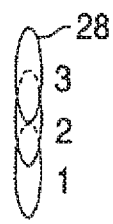
FIG. 6 is an axially-elongated plasma column produced in the focal zone by sequential application of a burst of pulses (1, 2, and 3) with a delay shorter than the plasma life time.
Figure 7A:
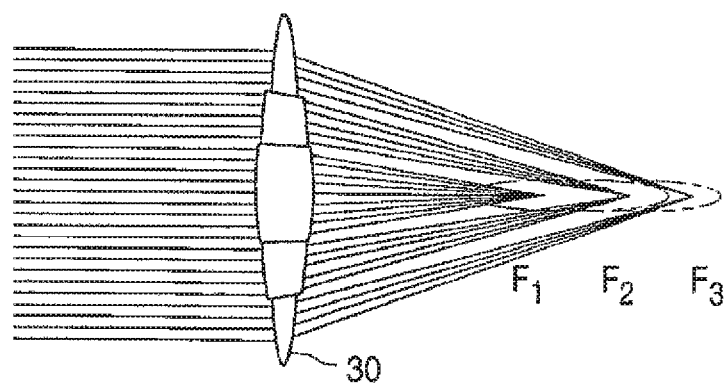
FIGS. 7A-7B are multi-segmented lenses for focusing the laser beam into 3 points along the same axis.
Figure 7B:
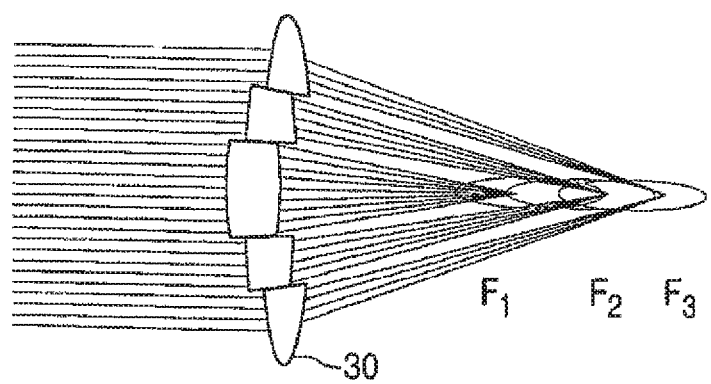
Figure 7C:
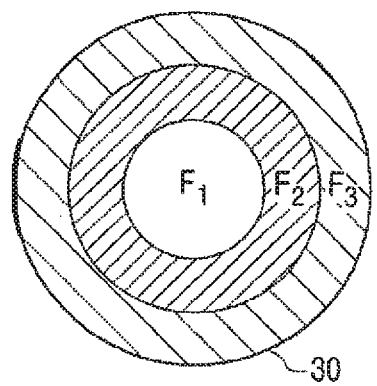
FIGS. 7C-7D are multi-segmented lenses with co-axial and off-axial segments having focal points along the same axis but different focal distances F1, F2, F3.
Figure 7D:
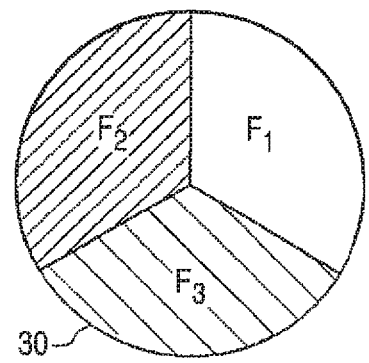
Figure 8:
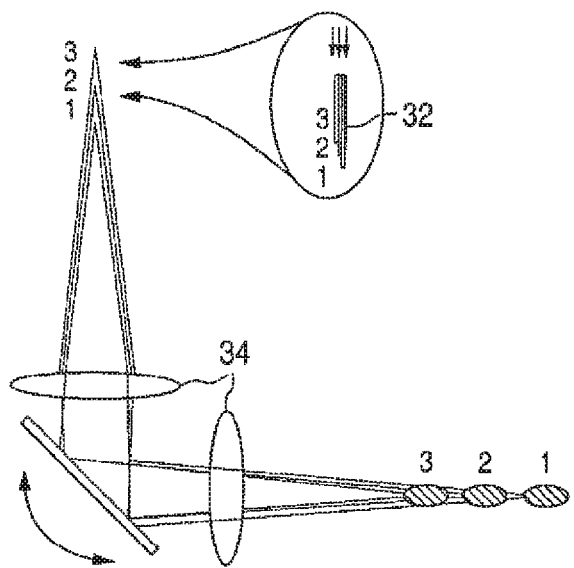
FIG. 8 is an axial array of fibers (1, 2, 3) focused with a set of lenses into multiple points (1, 2, 3) and thus producing plasma at different depths inside the tissue (1, 2, 3).

2) Producing axially-elongated rupture zones at fixed points by:

a) Using a sequence of 2-3 pulses in each spot separated by a few ps. Each pulse will be absorbed by the plasma 28 produced by the previous pulse and thus will extend the plasma 28 upwards along the beam as illustrated in FIG. 6A. In this approach, the laser energy should be 2 or 3 times higher, i.e. 20-30 µJ. Delay between the consecutive pulses should be longer than the plasma formation time (on the order of 0.1 ps) but not exceed the plasma recombination time (on the order of nanoseconds)

b) Producing an axial sequence of pulses with slightly different focusing points using multiple co-axial beams with different pre-focusing or multifocal optical elements. This can be achieved by using multi-focal optical elements (lenses, mirrors, diffractive optics, etc.). For example, a multi-segmented lens 30 can be used to focus the beam into multiple points (e.g. three separate points) along the same axis, using for example co-axial (see FIGS. 7A-7C) or off-coaxial (see FIG. 7D) segments to produce varying focal lengths (e.g. $F_1$, $F_2$, $F_3$). The multi-focal element 30 can be co-axial, or off-axis-segmented, or diffractive. Co-axial elements may have more axially-symmetric focal points, but will have different sizes due to the differences in beam diameters in each segment. Off-axial elements might have less symmetric focal points but all the elements can produce the foci of the same sizes.

c) Producing an elongated focusing column (as opposed to just a discrete number of focal points) using: (1) non-spherical (aspherical) optics, or (2) utilizing spherical aberrations in a lens with a high F number, or (3) diffractive optical element (hologram).

d) Producing an elongated zone of ionization using multiple optical fibers. For example, an array of optical fibers 32 of different lengths can be imaged with a set of lenses 34 into multiple focal points at different depths inside the tissue as shown in FIG. 8.

Figure 9A:
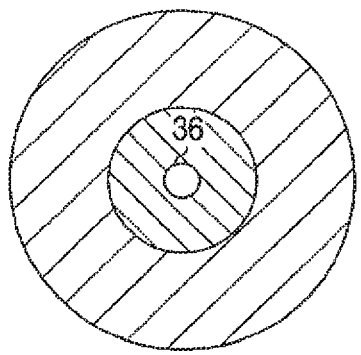
FIG. 9A and FIG. 9B are diagrams illustrating examples of the patterns that can be applied for nucleus segmentation.
Figure 9B:
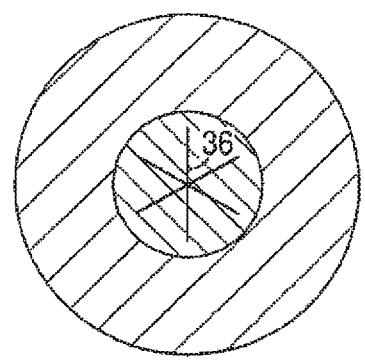
Figures 10A, 10B, 10C:
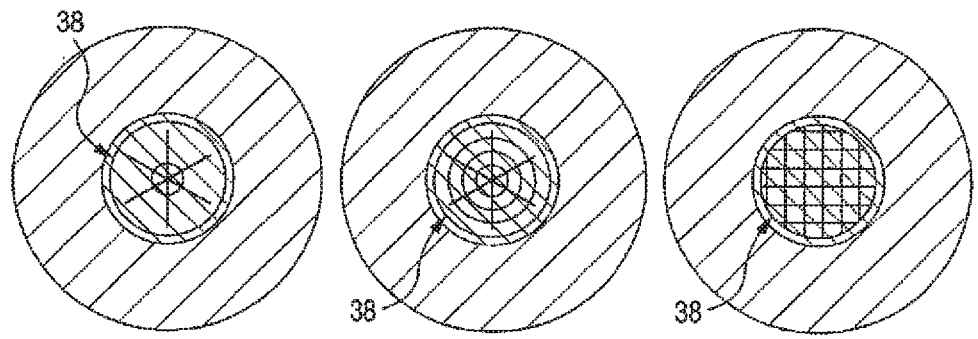
FIG. 10A-C is a planar view of some of the combined patterns for segmented capsulotomy and phaco-fragmentation.

Patterns of Scanning:

For anterior and posterior capsulotomy, the scanning patterns can be circular and spiral, with a vertical step similar to the length of the rupture zone. For segmentation of the eye lens 3, the patterns can be linear, planar, radial, radial segments, circular, spiral, curvilinear and combinations thereof including patterning in two and/or three dimensions. Scans can be continuous straight or curved lines, or one or more overlapping or spaced apart spots and/or line segments. Several scan patterns 36 are illustrated in FIGS. 9A and 9B, and combinations of scan patterns 38 are illustrated in FIGS. 10A-10C. Beam scanning with the multifocal focusing and/or patterning systems is particularly advantageous to successful lens segmentation since the lens thickness is much larger than the length of the beam waist axial. In addition, these and other 2D and 3D patterns may be used in combination with OCT to obtain additional imaging, anatomical structure or make-up (i.e., tissue density) or other dimensional information about the eye including but not limited to the lens, the cornea, the retina and as well as other portions of the eye.

The exemplary patterns allow for dissection of the lens cortex and nucleus into fragments of such dimensions that they can be removed simply with an aspiration needle, and can be used alone to perform capsulotomy. Alternatively, the laser patterning may be used to pre-fragment or segment the nucleus for later conventional ultrasonic phacoemulsification. In this case however, the conventional phacoemulsification would be less than a typical phacoemulsification performed in the absence of the inventive segmenting techniques because the lens has been segmented. As such, the phacoemulsification procedure would likely require less ultrasonic energy to be applied to the eye, allowing for a shortened procedure or requiring less surgical dexterity.

Complications due to the eye movements during surgery can be reduced or eliminated by performing the patterned laser cutting very rapidly (e.g. within a time period that is less than the natural eye fixation time). Depending on the laser power and repetition rate, the patterned cutting can be completed between 5 and 0.5 seconds (or even less), using a laser repetition rate exceeding 1 kHz.

The techniques described herein may be used to perform new ophthalmic procedures or improve existing procedures, including anterior and posterior capsulotomy, lens fragmentation and softening, dissection of tissue in the posterior pole (floaters, membranes, retina), as well as incisions in other areas of the eye such as, but not limited to, the sclera and iris.

Damage to an IOL during posterior capsulotomy can be reduced or minimized by advantageously utilizing a laser pattern initially focused beyond the posterior pole and then gradually moved anteriorly under visual control by the surgeon alone or in combination with imaging data acquired using the techniques described herein.

For proper alignment of the treatment beam pattern, an alignment beam and/or pattern can be first projected onto the target tissue with visible light (indicating where the treatment pattern will be projected. This allows the surgeon to adjust the size, location and shape of the treatment pattern. Thereafter, the treatment pattern can be rapidly applied to the target tissue using an automated 3 dimensional pattern generator (in the control electronics 12) by a short pulsed cutting laser having high repetition rate.

In addition, and in particular for capsulotomy and nuclear fragmentation, an automated method employing an imaging modality can be used, such as for example, electro-optical, OCT, acoustic, ultrasound or other measurement, to first ascertain the maximum and minimum depths of cutting as well as the size and optical density of the cataract nucleus. Such techniques allow the surgeon account for individual differences in lens thickness and hardness, and help determine the optimal cutting contours in patients. The system for measuring dimensions of the anterior chamber using OCT along a line, and/or pattern (2D or 3D or others as described herein) can be integrally the same as the scanning system used to control the laser during the procedure. As such, the data including, for example, the upper and lower boundaries of cutting, as well as the size and location of the nucleus, can be loaded into the scanning system to automatically determine the parameters of the cutting (i.e., segmenting or fracturing) pattern. Additionally, automatic measurement (using an optical, electro-optical, acoustic, or OCT device, or some combination of the above) of the absolute and relative positions and/or dimensions of a structure in the eye (e.g. the anterior and posterior lens capsules, intervening nucleus and lens cortex) for precise cutting, segmenting or fracturing only the desired tissues (e.g. lens nucleus, tissue containing cataracts, etc.) while minimizing or avoiding damage to the surrounding tissue can be made for current and/or future surgical procedures. Additionally, the same ultrashort pulsed laser can be used for imaging at a low pulse energy, and then for surgery at a high pulse energy.

Figure 11:
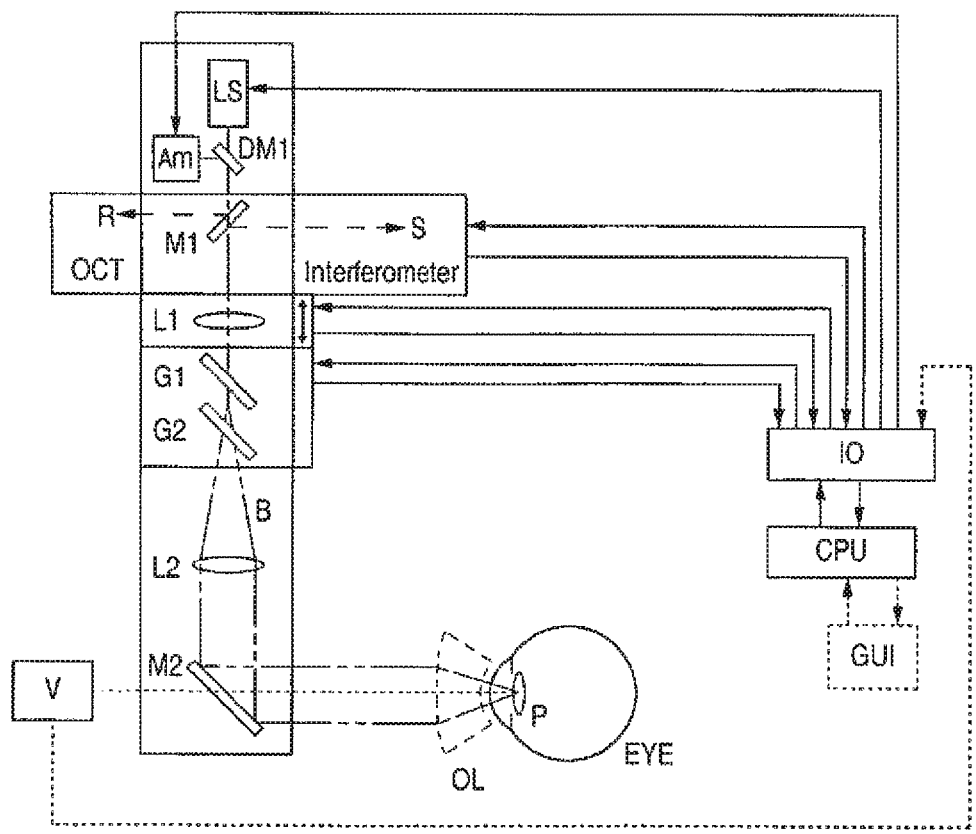
FIG. 11 is a plan diagram of one system embodiment that projects or scans an optical beam into a patient's eye.

The use of an imaging device to guide the treatment beam may be achieved many ways, such as those mentioned above as well as additional examples explained next (which all function to characterize tissue, and continue processing it until a target is removed). For example, in FIG. 11, a laser source LS and (optional) aiming beam source AIM have outputs that are combined using mirror DM1 (e.g. dichroic mirror). In this configuration, laser source LS may be used for both therapeutics and diagnostics. This is accomplished by means of mirror M1 which serves to provide both reference input R and sample input S to an OCT Interferometer by splitting the light beam B (centerlines shown) from laser source LS. Because of the inherent sensitivity of OCT Interferometers, mirror M1 may be made to reflect only a small portion of the delivered light. Alternatively, a scheme employing polarization sensitive pickoff mirrors may be used in conjunction with a quarter wave plate (not shown) to increase the overall optical efficiency of the system. Lens L1 may be a single element or a group of elements used to adjust the ultimate size or location along the z-axis of the beam B disposed to the target at point P. When used in conjunction with scanning in the X & Y axes, this configuration enables 3-dimensional scanning and/or variable spot diameters (i.e. by moving the focal point of the light along the z-axis).

In this example, transverse (XY) scanning is achieved by using a pair of orthogonal galvanometric mirrors G1 & G2 which may provide 2-dimensional random access scanning of the target. It should be noted that scanning may be achieved in a variety of ways, such as moving mirror M2, spinning polygons, translating lenses or curved mirrors, spinning wedges, etc. and that the use of galvanometric scanners does not limit the scope of the overall design. After leaving the scanner, light encounters lens L2 which serves to focus the light onto the target at point P inside the patient's eye EYE. An optional ophthalmic lens OL may be used to help focus the light. Ophthalmic lens OL may be a contact lens and further serve to dampen any motion of eye EYE, allowing for more stable treatment. Lens L2 may be made to move along the z-axis in coordination with the rest of the optical system to provide for 3-dimensional scanning, both for therapy and diagnosis. In the configuration shown, lens L2 ideally is moved along with the scanner G1 & G2 to maintain telecentricity. With that in mind, one may move the entire optical assembly to adjust the depth along the z-axis. If used with ophthalmic lens OL, the working distance may be precisely held. A device such as the Thorlabs EAS504 precision stepper motor can be used to provide both the length of travel as well as the requisite accuracy and precision to reliably image and treat at clinically meaningful resolutions. As shown it creates a telecentric scan, but need not be limited to such a design.

Mirror M2 serves to direct the light onto the target, and may be used in a variety of ways. Mirror M2 could be a dichroic element that the user looks through in order to visualize the target directly or using a camera, or may be made as small as possible to provide an opportunity for the user to view around it, perhaps with a binocular microscope. If a dichroic element is used, it may be made to be photopically neutral to avoid hindering the user's view. An apparatus for visualizing the target tissue is shown schematically as element V, and is preferably a camera with an optional light source for creating an image of the target tissue. The optional aiming beam AIM may then provide the user with a view of the disposition of the treatment beam, or the location of the identified targets. To display the target only, AIM may be pulsed on when the scanner has positioned it over an area deemed to be a target. The output of visualization apparatus V may be brought back to the system via the input/output device IO and displayed on a screen, such as a graphical user interface GUI. In this example, the entire system is controlled by the controller CPU, and data moved through input/output device IO. Graphical user interface GUI may be used to process user input, and display the images gathered by both visualization apparatus V and the OCT interferometer. There are many possibilities for the configuration of the OCT interferometer, including time and frequency domain approaches, single and dual beam methods, etc, as described in U.S. Pat. Nos. 5,748,898; 5,748, 352; 5,459,570; 6,111,645; and 6,053,613 (which are incorporated herein by reference.

Information about the lateral and axial extent of the cataract and localization of the boundaries of the lens capsule will then be used for determination of the optimal scanning pattern, focusing scheme, and laser parameters for the fragmentation procedure. Much if not all of this information can be obtained from visualization of the target tissue. For example, the axial extent of the fragmentation zone of a single pulse should not exceed the distance between (a) the cataract and the posterior capsule, and (b) the anterior capsule and the corneal endothelium. In the cases of a shallow anterior chamber and/or a large cataract, a shorter fragmentation zone should be selected, and thus more scanning planes will be required. Conversely, for a deep anterior chamber and/or a larger separation between the cataract and the posterior capsule a longer fragmentation zone can be used, and thus less planes of scanning will be required. For this purpose an appropriate focusing element will be selected from an available set. Selection of the optical element will determine the width of the fragmentation zone, which in turn will determine the spacing between the consecutive pulses. This, in turn, will determine the ratio between the scanning rate and repetition rate of the laser pulses. In addition, the shape of the cataract will determine the boundaries of the fragmentation zone and thus the optimal pattern of the scanner including the axial and lateral extent of the fragmentation zone, the ultimate shape of the scan, number of planes of scanning, etc.

Figure 12:
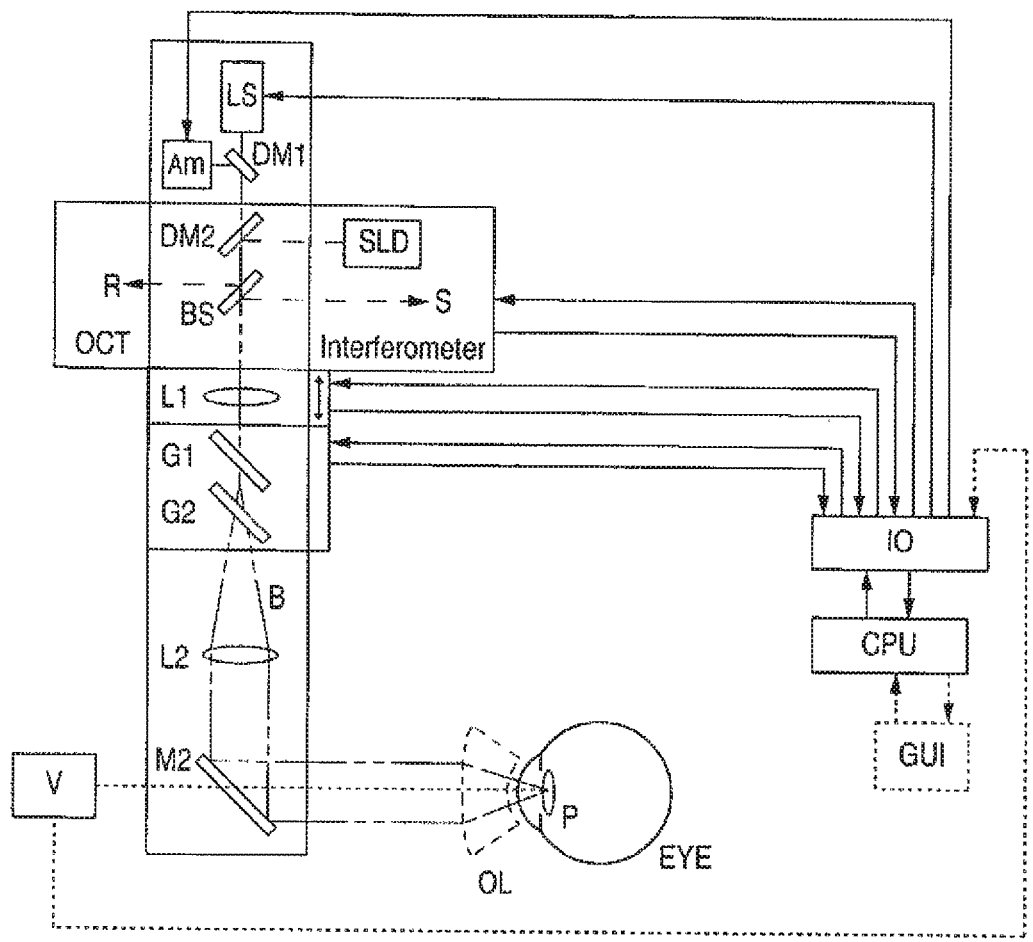
FIG. 12 is a plan diagram of another system embodiment that projects or scans an optical beam into a patient's eye.

FIG. 12 shows an alternate embodiment in which the imaging and treatment sources are different. A dichroic mirror DM2 has been added to the configuration of FIG. 11 to combine the imaging and treatment light, and mirror M1 has been replaced by beam splitter BS which is highly transmissive at the treatment wavelength, but efficiently separates the light from the imaging source SLD for use in the OCT Interferometer. Imaging source SLD may be a superluminescent diode having a spectral output that is nominally 50 nm wide, and centered on or around 835 nm, such as the SuperLum SLD-37. Such a light source is well matched to the clinical application, and sufficiently spectrally distinct from the treatment source, thus allowing for elements DM and BS to be reliably fabricated without the necessarily complicated and expensive optical coatings that would be required if the imaging and treatment sources were closer in wavelength.

Figure 13:
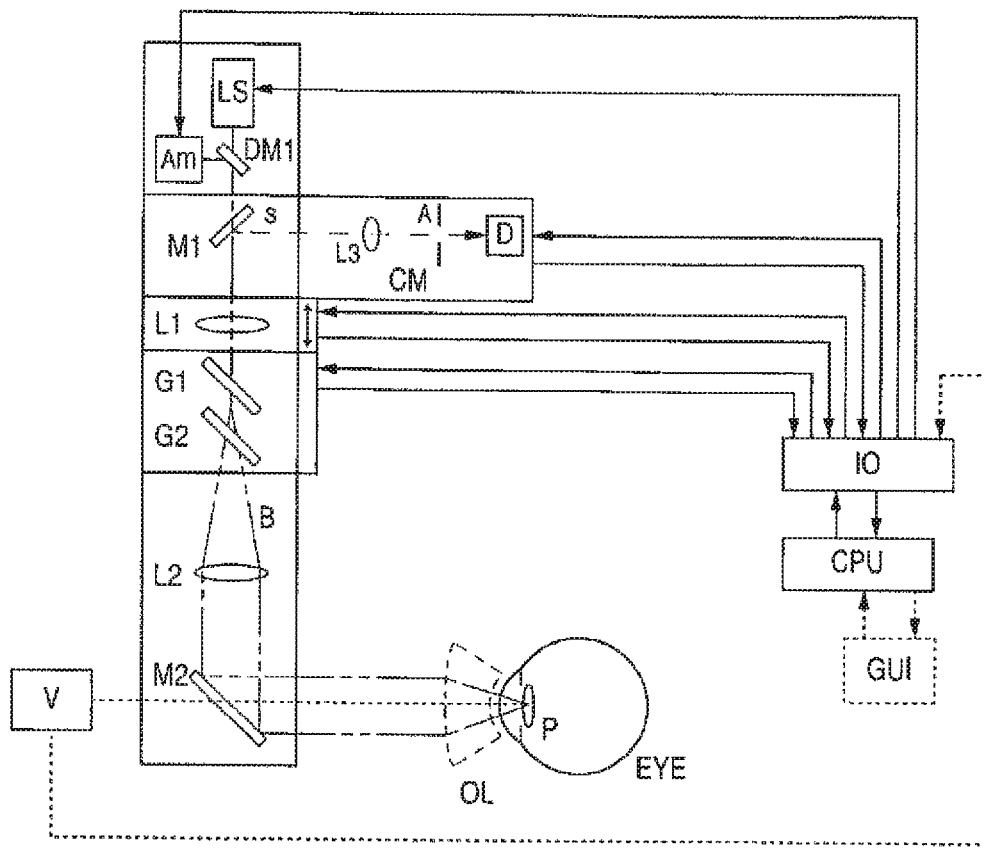
FIG. 13 is a plan diagram of yet another system embodiment that projects or scans an optical beam into a patient's eye.

FIG. 13 shows an alternate embodiment incorporating a confocal microscope CM for use as an imaging system. In this configuration, mirror M1 reflects a portion of the backscattered light from beam B into lens L3. Lens L3 serves to focus this light through aperture A (serving as a spatial filter) and ultimately onto detector D. As such, aperture A and point P are optically conjugate, and the signal received by detector D is quite specific when aperture A is made small enough to reject substantially the entire background signal. This signal may thus be used for imaging, as is known in the art. Furthermore, a fluorophore may be introduced into the target to allow for specific marking of either target or healthy tissue. In this approach, the ultrafast laser may be used to pump the absorption band of the fluorophore via a multiphoton process or an alternate source (not shown) could be used in a manner similar to that of FIG. 12.

Figure 14:
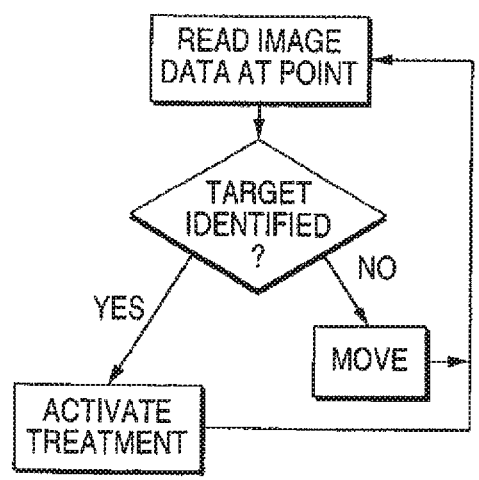
FIG. 14 is a flow diagram showing the steps utilized in a "track and treat" approach to material removal.

FIG. 14 is a flowchart outlining the steps utilized in a "track and treat" approach to material removal. First an image is created by scanning from point to point, and potential targets identified. When the treatment beam is disposed over a target, the system can transmit the treatment beam, and begin therapy. The system may move constantly treating as it goes, or dwell in a specific location until the target is fully treated before moving to the next point.

Figure 15:
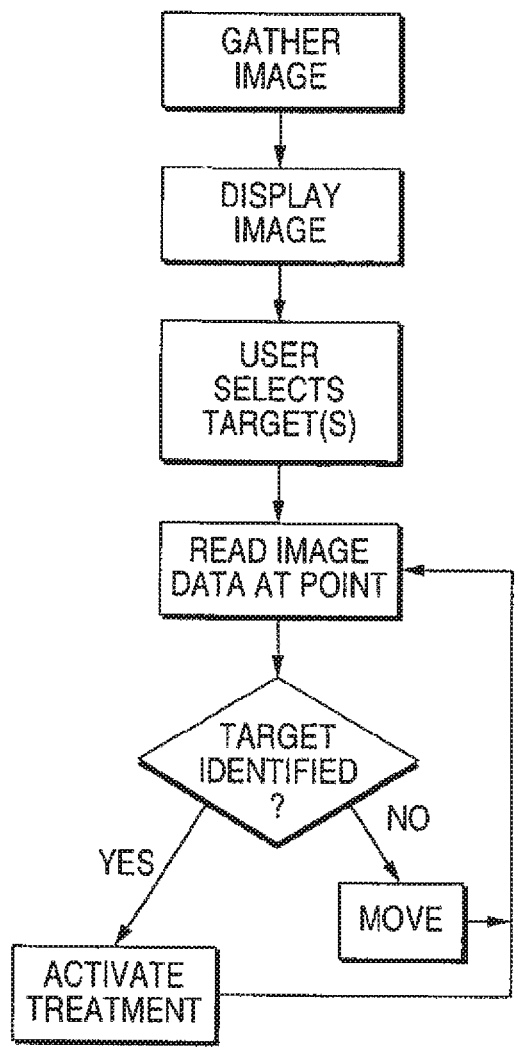
FIG. 15 is a flow diagram showing the steps utilized in a "track and treat" approach to material removal that employs user input.

The system operation of FIG. 14 could be modified to incorporate user input. As shown in FIG. 15, a complete image is displayed to the user, allowing them to identify the target(s). Once identified, the system can register subsequent images, thus tracking the user defined target(s). Such a registration scheme may be implemented in many different ways, such as by use of the well known and computationally efficient Sobel or Canny edge detection schemes. Alternatively, one or more readily discernable marks may be made in the target tissue using the treatment laser to create a fiduciary reference without patient risk (since the target tissue is destined for removal).

In contrast to conventional laser techniques, the above techniques provide (a) application of laser energy in a pattern, (b) a high repetition rate so as to complete the pattern within the natural eye fixation time, (c) application of sub-ps pulses to reduce the threshold energy, and (d) the ability to integrate imaging and treatment for an automated procedure.

Laser Delivery System

The laser delivery system in FIG. 1 can be varied in several ways. For example, the laser source could be provided onto a surgical microscope, and the microscope's optics used by the surgeon to apply the laser light, perhaps through the use of a provided console. Alternately, the laser and delivery system would be separate from the surgical microscope and would have an optical system for aligning the aiming beam for cutting. Such a system could swing into position using an articulating arm attached to a console containing the laser at the beginning of the surgery, and then swing away allowing the surgical microscope to swing into position.

The pattern to be applied can be selected from a collection of patterns in the control electronics 12, produced by the visible aiming beam, then aligned by the surgeon onto the target tissue, and the pattern parameters (including for example, size, number of planar or axial elements, etc.) adjusted as necessary for the size of the surgical field of the particular patient (level of pupil dilation, size of the eye, etc.). Thereafter, the system calculates the number of pulses that should be applied based on the size of the pattern. When the pattern calculations are complete, the laser treatment may be initiated by the user (i.e., press a pedal) for a rapid application of the pattern with a surgical laser.

The laser system can automatically calculate the number of pulses required for producing a certain pattern based on the actual lateral size of the pattern selected by surgeon. This can be performed with the understanding that the rupture zone by the single pulse is fixed (determined by the pulse energy and configuration of the focusing optics), so the number of pulses required for cutting a certain segment is determined as the length of that segment divided by the width of the rupture zone by each pulse. The scanning rate can be linked to the repetition rate of the laser to provide a pulse spacing on tissue determined by the desired distance. The axial step of the scanning pattern will be determined by the length of the rupture zone, which is set by the pulse energy and the configuration of the focusing optics.

Fixation Considerations

The methods and systems described herein can be used alone or in combination with an aplanatic lens (as described in, for example, the U.S. Pat. No. 6,254,595, incorporated herein by reference) or other device to configure the shape of the cornea to assist in the laser methods described herein. A ring, forceps or other securing means may be used to fixate the eye when the procedure exceeds the normal fixation time of the eye. Regardless whether an eye fixation device is used, patterning and segmenting methods described herein may be further subdivided into periods of a duration that may be performed within the natural eye fixation time.

Another potential complication associated with a dense cutting pattern of the lens cortex is the duration of treatment: If a volume of 6×6×4 mm=144 $mm^3$ of lens is segmented, it will require N=722,000 pulses. If delivered at 50 kHz, it will take 15 seconds, and if delivered at 10 kHz it will take 72 seconds. This is much longer than the natural eye fixation time, and it might require some fixation means for the eye. Thus, only the hardened nucleus may be chosen to be segmented to ease its removal. Determination of its boundaries with the OCT diagnostics will help to minimize the size of the segmented zone and thus the number of pulses, the level of cumulative heating, and the treatment time. If the segmentation component of the procedure duration exceeds the natural fixation time, then the eye may be stabilized using a conventional eye fixation device.

Thermal Considerations

In cases where very dense patterns of cutting are needed or desired, excess accumulation of heat in the lens may damage the surrounding tissue. To estimate the maximal heating, assume that the bulk of the lens is cut into cubic pieces of 1 mm in size. If tissue is dissected with $E_1$=10 uJ pulses fragmenting a volume of 15 um in diameter and 200 um in length per pulse, then pulses will be applied each 15 um. Thus a 1×1 mm plane will require 66×66=4356 pulses. The 2 side walls will require 2×66×5=660 pulses, thus total N=5016 pulses will be required per cubic mm of tissue. Since all the laser energy deposited during cutting will eventually be transformed into heat, the temperature elevation will be DT=($E_1$*N)/pcV=50.16 mJ/(4.19 mJ/K)=12 K. This will lead to maximal temperature T=37+12° C.=49° C. This heat will dissipate in about one minute due to heat diffusion. Since peripheral areas of the lens will not be segmented (to avoid damage to the lens capsule) the average temperature at the boundaries of the lens will actually be lower. For example, if only half of the lens volume is fragmented, the average temperature elevation at the boundaries of the lens will not exceed 6° C. (T=43° C.) and on the retina will not exceed 0.1 C. Such temperature elevation can be well tolerated by the cells and tissues. However, much higher temperatures might be dangerous and should be avoided.

To reduce heating, a pattern of the same width but larger axial length can be formed, so these pieces can still be removed by suction through a needle. For example, if the lens is cut into pieces of 1×1×4 mm in size, a total of N=6996 pulses will be required per 4 cubic mm of tissue. The temperature elevation will be DT=($E_1$*N)/pcV=69.96 mJ/(4.19 mJ/K)/4=1.04 K. Such temperature elevation can be well tolerated by the cells and tissues.

An alternative solution to thermal limitations can be the reduction of the total energy required for segmentation by tighter focusing of the laser beam. In this regime a higher repetition rate and low pulse energy may be used. For example, a focal distance of F=50 mm and a beam diameter of $D_b$=10 mm would allow for focusing into a spot of about 4 μm in diameter. In this specific example, repetition rate of about 32 kHz provides an 8 mm diameter circle in about 0.2 s.

To avoid retinal damage due to explosive vaporization of melanosomes following absorption of the short laser pulse the laser radiant exposure on the RPE should not exceed 100 mJ/cm$^2$. Thus NA of the focusing optics should be adjusted such that laser radiant exposure on the retina will not exceed this safety limit. With a pulse energy of 10 μJ, the spot size on retina should be larger than 0.1 mm in diameter, and with a 1 mJ pulse it should not be smaller than 1 mm. Assuming a distance of 20 mm between lens and retina, these values correspond to minimum numerical apertures of 0.0025 and 0.025, respectively.

To avoid thermal damage to the retina due to heat accumulation during the lens fragmentation the laser irradiance on the retina should not exceed the thermal safety limit for near-IR radiation—on the order of 0.6 W/cm$^2$. With a retinal zone of about 10 mm in diameter (8 mm pattern size on a lens+1 mm on the edges due to divergence) it corresponds to total power of 0.5 W on the retina.

Transverse Focal Volume

Figure 16:
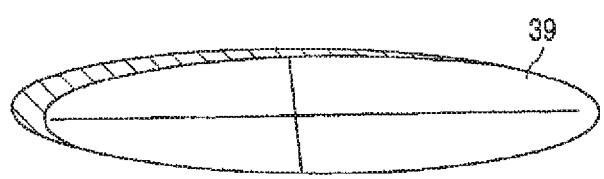
FIG. 16 is a perspective view of a transverse focal zone created by an anamorphic optical scheme.

It is also possible to create a transverse focal volume 50 instead of an axial focal volume described above. An anamorphic optical scheme may used to produce a focal zone 39 that is a "line" rather than a single point, as is typical with spherically symmetric elements (see FIG. 16). As is standard in the field of optical design, the term "anamorphic" is meant herein to describe any system which has different equivalent focal lengths in each meridian. It should be noted that any focal point has a discrete depth of field. However, for tightly focused beams, such as those required to achieve the electric field strength sufficient to disrupt biological material with ultrashort pulses (defined as $t_{pulse}$<10 ps), the depth of focus is proportionally short.

Figure 17A:
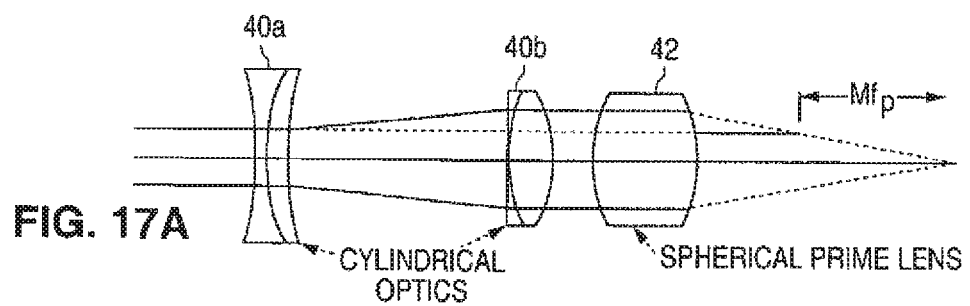
FIGS. 17A-17C are perspective views of an anamorphic telescope configuration for constructing an inverted Keplerian telescope.
Figure 17B:
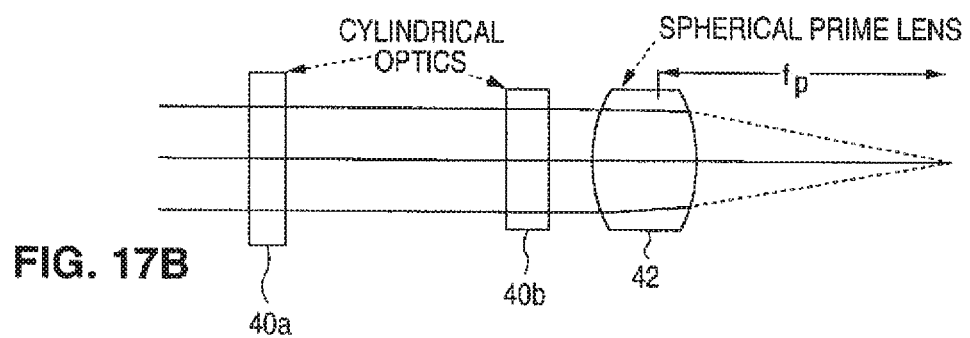
Figure 17C:
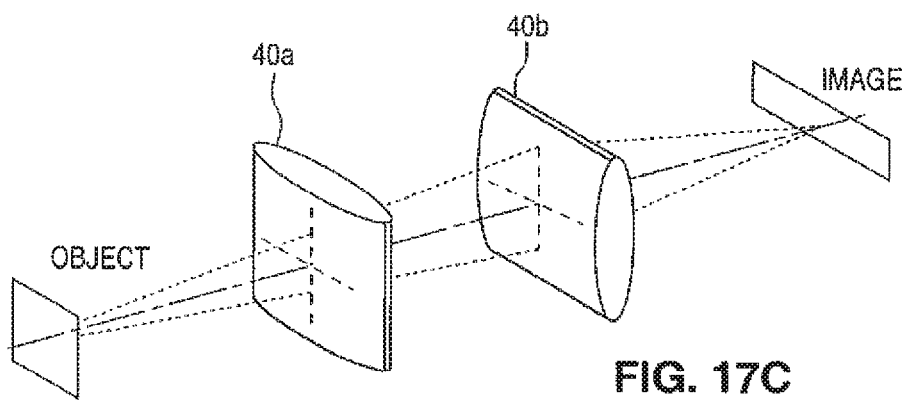

Such a 1-dimensional focus may be created using cylindrical lenses, and/or mirrors. An adaptive optic may also be used, such as a MEMS mirror or a phased array. When using a phased array, however, careful attention should be paid to the chromatic effects of such a diffractive device. FIGS. 17A-17C illustrate an anamorphic telescope configuration, where cylindrical optics 40a/b and spherical lens 42 are used to construct an inverted Keplerian telescope along a single meridian (see FIG. 17A) thus providing an elongated focal volume transverse to the optical axis (see FIG. 17C). Compound lenses may be used to allow the beam's final dimensions to be adjustable.

Figure 18:
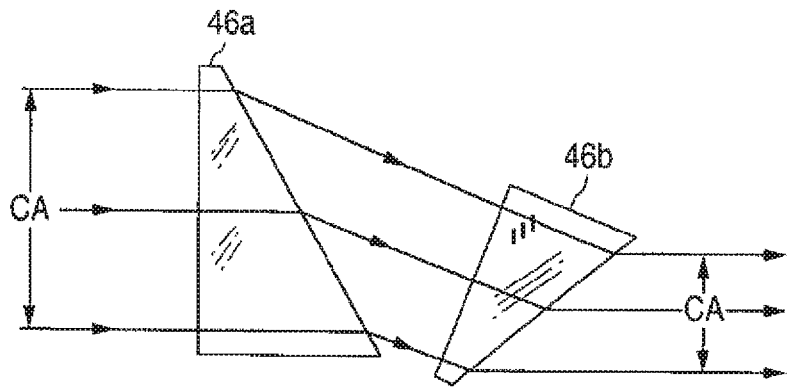
FIG. 18 is a side view of prisms used to extend the beam along a single meridian.

FIG. 18 shows the use of a pair of prisms 46a/b to extend the beam along a single meridian, shown as CA. In this example, CA is reduced rather than enlarged to create a linear focal volume.

The focus may also be scanned to ultimately produce patterns. To effect axial changes, the final lens may be made to move along the system's z-axis to translate the focus into the tissue. Likewise, the final lens may be compound, and made to be adjustable. The 1-dimensional focus may also be rotated, thus allowing it to be aligned to produce a variety of patterns, such as those shown in FIGS. 9 and 10. Rotation may be achieved by rotating the cylindrical element itself. Of course, more than a single element may be used. The focus may also be rotated by using an additional element, such as a Dove prism (not shown). If an adaptive optic is used, rotation may be achieved by rewriting the device, thus streamlining the system design by eliminating a moving part.

Figure 19:
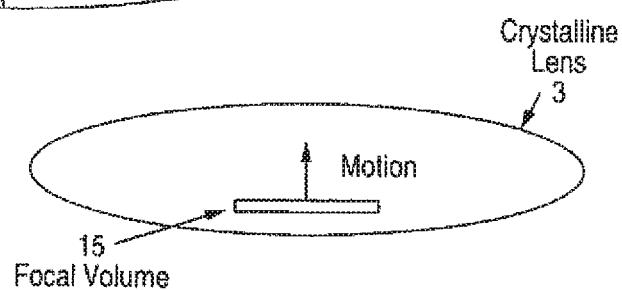
FIG. 19 is a top view illustrating the position and motion of a transverse focal volume on the eye lens.

The use of a transverse line focus allows one to dissect a cataractous lens by ablating from the posterior to the anterior portion of the lens, thus planing it. Furthermore, the linear focus may also be used to quickly open the lens capsule, readying it for extraction. It may also be used for any other ocular incision, such as the conjunctiva, etc. (see FIG. 19).

Cataract Removal Using a Track and Treat Approach

A "track and treat" approach is one that integrates the imaging and treatment aspect of optical eye surgery, for providing an automated approach to removal of debris such as cataractous and cellular material prior to the insertion of an IOL. An ultrafast laser is used to fragment the lens into pieces small enough to be removed using an irrigating/aspirating probe of minimal size without necessarily rupturing the lens capsule. An approach such as this that uses tiny, self-sealing incisions may be used to provide a capsule for filling with a gel or elastomeric IOL. Unlike traditional hard IOLS that require large incisions, a gel or liquid may be used to fill the entire capsule, thus making better use of the body's own accommodative processes. As such, this approach not only addresses cataract, but presbyopia as well.

Alternately, the lens capsule can remain intact, where bilateral incisions are made for aspirating tips, irrigating tips, and ultrasound tips for removing the bulk of the lens. Thereafter, the complete contents of the bag/capsule can be successfully rinsed/washed, which will expel the debris that can lead to secondary cataracts. Then, with the lens capsule intact, a minimal incision is made for either a foldable IOL or optically transparent gel injected through incision to fill the bag/capsule. The gel would act like the natural lens with a larger accommodating range.

It is to be understood that the present invention is not limited to the embodiment(s) described above and illustrated herein, but encompasses any and all variations falling within the scope of the appended claims. For example, materials, processes and numerical examples described above are exemplary only, and should not be deemed to limit the claims. Multi-segmented lens 30 can be used to focus the beam simultaneously at multiple points not axially overlapping (i.e. focusing the beam at multiple foci located at different lateral locations on the target tissue). Further, as is apparent from the claims and specification, not all method steps need be performed in the exact order illustrated or claimed, but rather in any order that accomplishes the goals of the surgical procedure.

DETAILED DESCRIPTION OF THE INVENTION

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A laser surgical system for making incisions in ocular tissues during a cataract surgical procedure, the system comprising:
    a laser system comprising a scanning assembly, a laser operable to generate a laser beam configured to incise ocular tissue;
    an imaging device configured to acquire image data from locations distributed throughout a volume of a crystalline lens of the patient and construct one or more images of the patient's eye tissues from the image data, wherein the one or more images comprise an image of at least a portion of the crystalline lens; and
    a control system operably coupled to the laser system and configured to:
        operate the imaging device to generate image data of a continuous depth profile of the volume of the patient's crystalline lens;
        identify one or more boundaries of the one or more tissue structures of the crystalline lens based at least in part on the image data;
        process the image data to determine a lens fragmentation treatment region of the lens of the eye based at least in part upon the one or more boundaries, the lens fragmentation treatment region comprising a posterior cutting boundary located anterior to the posterior capsule of the lens;
        process the image data to determine a lens fragmentation scanning pattern for scanning a focal zone of the laser beam for performing lens fragmentation, the lens fragmentation pattern comprising a scanning pattern at a plurality of depths within the lens fragmentation treatment region; and
        operate the laser and the scanning assembly to scan the focal zone of the laser beam in the lens fragmentation scanning pattern consecutively at each of the plurality of depths within the lens fragmentation treatment region,
    wherein positioning of the focal zone is guided by the control system based on the image data.

2. The system of claim 1, wherein the imaging device is an optical coherence tomography system.

3. The system of claim 1, wherein the lens fragmentation treatment region does not transect the posterior capsule.

4. The system of claim 1, wherein all scanning of the focal zone occurs anterior to the posterior capsule.

5. The system of claim 1, further comprising a user interface, under operative control of the controller, configure to receive user input comprising one or more parameters used in scanning the eye tissue.

6. The system of claim 1, wherein the imaging device comprises at least one of a camera, an interferometer, a time domain optical coherence tomography system, a frequency domain optical tomography system, a confocal microscope, and a scanning confocal microscope.

7. The system of claim 6, wherein the imaging device is a camera.

8. The system of claim 1, wherein the scanning pattern is selected from the group consisting of: two or more intersecting straight lines, a crosshatched pattern comprising two or more sets of intersecting lines, one or more curved lines, a circular line, two or more concentric circular lines, and one or more spiral-shaped lines.

9. The system of claim 1, wherein the lens is fragmented into segments that can be removed through a lumen of an ophthalmic aspiration probe.

10. A laser surgical system for making incisions in ocular tissues during a cataract surgical procedure, the system comprising:
    a laser system comprising a scanning assembly, a laser operable to generate a laser beam configured to incise ocular tissue;
    an imaging device configured to acquire image data from locations distributed throughout a volume of a crystalline lens of the patient and construct one or more images of the patient's eye tissues from the image data, wherein the one or more images comprise an image of at least a portion of the crystalline lens; and
    a control system operably coupled to the laser system and configured to:
        operate the imaging device to generate image data of a continuous depth profile of the volume of the patient's crystalline lens;
        identify one or more boundaries of the one or more tissue structures of the crystalline lens based at least in part on the image data;
        process the image data to determine a lens fragmentation treatment region of the lens of the eye based at least in part upon the one or more boundaries; and
        operate the laser and the scanning assembly to scan the focal zone of the laser beam in a treatment scanning pattern to effect 3-dimensional patterned laser cutting of the crystalline lens within the lens fragmentation cutting region into a plurality of segments or pieces for subsequent removal,
    wherein positioning of the focal zone is guided by the control system based on the image data.

11. The system of claim 10, wherein the imaging device is an optical coherence tomography system.

12. The system of claim 10, wherein the lens fragmentation treatment region does not transect the posterior capsule.

13. The system of claim 10, wherein all scanning of the focal zone occurs anterior to the posterior capsule.

14. The system of claim 10, further comprising a user interface, under operative control of the controller, configure to receive user input comprising one or more parameters used in scanning the eye tissue.

15. The system of claim 10, wherein the imaging device comprises at least one of a camera, an interferometer, a time domain optical coherence tomography system, a frequency domain optical tomography system, a confocal microscope, and a scanning confocal microscope.

16. The system of claim 15, wherein the imaging device is a camera.

17. The system of claim 10, wherein the scanning pattern is selected from the group consisting of: two or more intersecting straight lines, a crosshatched pattern comprising two or more sets of intersecting lines, one or more curved lines, a circular line, two or more concentric circular lines, and one or more spiral-shaped lines.

18. The system of claim 11, wherein the lens is fragmented into segments that can be removed through a lumen of an ophthalmic aspiration probe.

* * * * *

(12) INTER PARTES REVIEW CERTIFICATE (3072nd)
United States Patent
Palanker et al.

(10) Number: US 9,693,903 K1
(45) Certificate Issued: Apr. 4, 2023

(54) APPARATUS FOR PATTERNED PLASMA-MEDIATED LASER OPHTHALMIC SURGERY

(71) Applicants: Daniel V. Palanker; Mark S. Blumenkranz; David H. Mordaunt; Dan E. Andersen

(72) Inventors: Daniel V. Palanker; Mark S. Blumenkranz; David H. Mordaunt; Dan E. Andersen

(73) Assignee: OPTIMEDICA CORPORATION

Trial Number:

IPR2021-00824 filed Apr. 17, 2021

Inter Partes Review Certificate for:

Patent No.: 9,693,903
Issued: Jul. 4, 2017
Appl. No.: 15/236,284
Filed: Aug. 12, 2016

The results of IPR2021-00824 are reflected in this inter partes review certificate under 35 U.S.C. 318(b).

INTER PARTES REVIEW CERTIFICATE
U.S. Patent 9,693,903 K1
Trial No. IPR2021-00824
Certificate Issued Apr. 4, 2023

AS A RESULT OF THE INTER PARTES REVIEW PROCEEDING, IT HAS BEEN DETERMINED THAT:

Claims 1-6, 8-15 and 17-18 are found patentable.

\* \* \* \* \*